(12) United States Patent
Zapol et al.

(10) Patent No.: US 10,646,682 B2
(45) Date of Patent: May 12, 2020

(54) INSPIRATORY SYNTHESIS OF NITRIC OXIDE

(71) Applicant: THE GENERAL HOSPITAL CORPORATION, Boston, MA (US)

(72) Inventors: Warren M. Zapol, Cambridge, MA (US); Binglan Yu, Lexington, MA (US); Paul Hardin, Lowell, MA (US); Matthew Hickcox, Groton, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 16/593,718

(22) Filed: Oct. 4, 2019

(65) Prior Publication Data

US 2020/0030567 A1   Jan. 30, 2020

Related U.S. Application Data

(63) Continuation of application No. 16/058,797, filed on Aug. 8, 2018, now Pat. No. 10,434,276, which is a
(Continued)

(51) Int. Cl.
*A61M 16/12* (2006.01)
*A61M 16/10* (2006.01)
(Continued)

(52) U.S. Cl.
CPC .......... *A61M 16/12* (2013.01); *A61M 15/02* (2013.01); *A61M 16/0003* (2014.02);
(Continued)

(58) Field of Classification Search
CPC .............. A61M 15/02; A61M 15/0016; A61M 15/0091; A61M 16/10; A61M 16/104; A61M 2016/0015; A61M 2202/0275
See application file for complete search history.

(56) References Cited

U.S. PATENT DOCUMENTS 2,485,481 A   10/1949   Cotton
2,525,938 A   10/1950   Peck
(Continued)

FOREIGN PATENT DOCUMENTS

CN   1099997 A   3/1995
CN   1730115 A   2/2006
(Continued)

OTHER PUBLICATIONS

Keshav, Using Plasmas for High-Speed Flow Control and Combustion Control, Dissertation for Degree of Doctor of Philosophy, The Ohio State University, 2008, 268 pages.
(Continued)

*Primary Examiner* — Michael J Tsai
(74) *Attorney, Agent, or Firm* — Quarles & Brady LLP

(57) ABSTRACT

A system for generating nitric oxide can include an apparatus positioned in a trachea of a mammal, the apparatus including a respiration sensor for collecting information related to one or more triggering events associated with the trachea, an oxygen sensor for collecting information related to a concentration of oxygen in a gas, and one or more pairs of electrodes for initiating a series of electric arcs to generate nitric oxide, and the system for generating nitric oxide can also include a controller for determining one or more control parameters based on the information collected by the respiration sensor and the oxygen sensor, wherein the series of electric arcs is initiated based on the control parameters determined by the controller.

20 Claims, 41 Drawing Sheets

Related U.S. Application Data continuation of application No. 14/777,072, filed as application No. PCT/US2014/028439 on Mar. 14, 2014, now Pat. No. 10,293,133.

(60) Provisional application No. 61/789,161, filed on Mar. 15, 2013, provisional application No. 61/792,473, filed on Mar. 15, 2013.

(51) Int. Cl.
| | |
|---|---|
| *C01B 21/20* | (2006.01) |
| *A61M 15/02* | (2006.01) |
| *A61M 16/00* | (2006.01) |
| *B01D 53/56* | (2006.01) |
| *A61M 16/04* | (2006.01) |
| *A61M 16/06* | (2006.01) |
| *A61M 16/20* | (2006.01) |

(52) U.S. Cl.
CPC .... *A61M 16/0063* (2014.02); *A61M 16/0072* (2013.01); *A61M 16/0465* (2013.01); *A61M 16/06* (2013.01); *A61M 16/10* (2013.01); *A61M 16/101* (2014.02); *A61M 16/20* (2013.01); *B01D 53/56* (2013.01); *C01B 21/203* (2013.01); *A61M 16/0057* (2013.01); *A61M 16/107* (2014.02); *A61M 16/108* (2014.02); *A61M 16/202* (2014.02); *A61M 16/209* (2014.02); *A61M 2016/0021* (2013.01); *A61M 2016/0033* (2013.01); *A61M 2016/1025* (2013.01); *A61M 2016/1035* (2013.01); *A61M 2202/0208* (2013.01); *A61M 2202/0216* (2013.01); *A61M 2202/0275* (2013.01); *A61M 2205/04* (2013.01); *A61M 2205/33* (2013.01); *A61M 2205/3303* (2013.01); *A61M 2205/3334* (2013.01); *A61M 2205/3553* (2013.01); *A61M 2205/3561* (2013.01); *A61M 2205/3569* (2013.01); *A61M 2205/3584* (2013.01); *A61M 2205/3592* (2013.01); *A61M 2205/366* (2013.01); *A61M 2205/3606* (2013.01); *A61M 2205/50* (2013.01); *A61M 2205/7545* (2013.01); *A61M 2210/1032* (2013.01); *A61M 2230/40* (2013.01); *B01D 2251/304* (2013.01); *B01D 2251/306* (2013.01); *B01D 2251/404* (2013.01)

(56) References Cited

U.S. PATENT DOCUMENTS

| | | | |
|---|---|---|---|
| 2,684,448 A | 7/1954 | Nilles, Jr. | |
| 3,225,309 A | 12/1965 | Phelps | |
| 4,287,040 A | 9/1981 | Alamaro | |
| 4,500,563 A | 2/1985 | Ellenberger et al. | |
| 4,505,795 A | 3/1985 | Alamaro | |
| 4,680,694 A | 7/1987 | Huynh et al. | |
| 4,695,358 A | 9/1987 | Mizuno et al. | |
| 4,705,670 A | 11/1987 | O'Hare | |
| 4,816,229 A | 3/1989 | Jensen et al. | |
| 4,877,589 A | 10/1989 | O'Hare | |
| 5,285,372 A | 2/1994 | Huynh et al. | |
| 5,378,436 A | 1/1995 | Endoh et al. | |
| 5,396,882 A | 3/1995 | Zapol | |
| 5,471,977 A | 12/1995 | Olsson et al. | |
| 5,485,827 A | 1/1996 | Zapol et al. | |
| 5,546,935 A | 8/1996 | Champeau | |
| 5,558,083 A | 9/1996 | Bathe et al. | |
| 5,573,733 A | 11/1996 | Salama | |
| 5,692,495 A | 12/1997 | Sheu | |
| 5,732,693 A | 3/1998 | Bathe et al. | |
| 5,752,504 A | 5/1998 | Bathe | |
| 5,839,433 A | 11/1998 | Higenbottam | |
| 5,845,633 A | 12/1998 | Psaros | |
| 6,089,229 A | 7/2000 | Bathe et al. | |
| 6,109,260 A | 8/2000 | Bathe | |
| 6,125,846 A | 10/2000 | Bathe et al. | |
| 6,164,276 A | 12/2000 | Bathe et al. | |
| 6,224,653 B1 | 5/2001 | Shvedchikov et al. | |
| 6,250,302 B1 | 6/2001 | Rantala | |
| 6,296,827 B1 | 10/2001 | Castor et al. | |
| 6,536,429 B1 | 3/2003 | Pavlov et al. | |
| 6,581,599 B1* | 6/2003 | Stenzler | A61M 16/203 128/204.23 |
| 6,668,828 B1* | 12/2003 | Figley | A61M 16/208 128/204.18 |
| 6,758,214 B2 | 7/2004 | Fine et al. | |
| 6,920,876 B2 | 7/2005 | Miller et al. | |
| 6,955,171 B1 | 10/2005 | Figley et al. | |
| 6,955,790 B2 | 10/2005 | Castor et al. | |
| 6,986,351 B2 | 1/2006 | Figley et al. | |
| 7,025,869 B2 | 4/2006 | Fine et al. | |
| 7,040,313 B2 | 5/2006 | Fine et al. | |
| 7,122,018 B2 | 10/2006 | Stenzler et al. | |
| 7,220,393 B2 | 5/2007 | Miller et al. | |
| 7,255,105 B2 | 8/2007 | Figley et al. | |
| 7,312,584 B2 | 12/2007 | Tamita et al. | |
| 7,335,181 B2 | 2/2008 | Miller et al. | |
| 7,485,324 B2 | 2/2009 | Miller et al. | |
| 7,498,000 B2 | 3/2009 | Pekshev et al. | |
| 7,516,742 B2 | 4/2009 | Stenzler et al. | |
| 7,520,866 B2 | 4/2009 | Stenzler et al. | |
| 7,531,133 B2 | 5/2009 | Hole et al. | |
| 7,560,076 B2 | 7/2009 | Rounbehler et al. | |
| 7,589,473 B2 | 9/2009 | Suslov | |
| 7,744,812 B2 | 6/2010 | Witherspoon et al. | |
| 7,861,717 B1 | 1/2011 | Krebs | |
| 7,955,294 B2 | 6/2011 | Stenzler et al. | |
| 8,030,849 B2 | 10/2011 | Suslov | |
| 8,043,252 B2 | 10/2011 | Miller et al. | |
| 8,079,998 B2 | 12/2011 | Hole et al. | |
| 8,151,791 B2 | 4/2012 | Arlow et al. | |
| 8,282,966 B2 | 10/2012 | Baldassarre et al. | |
| 8,291,904 B2 | 10/2012 | Bathe et al. | |
| 8,293,284 B2 | 10/2012 | Baldassarre et al. | |
| 8,344,627 B1 | 1/2013 | Hooke et al. | |
| 8,431,163 B2 | 4/2013 | Baldassarre et al. | |
| 8,518,457 B2 | 8/2013 | Miller et al. | |
| 8,573,209 B2 | 11/2013 | Bathe et al. | |
| 8,573,210 B2 | 11/2013 | Bathe et al. | |
| 8,574,531 B2 | 11/2013 | Miller et al. | |
| 8,717,733 B2 | 5/2014 | Gefter et al. | |
| 8,770,199 B2* | 7/2014 | Flanagan | A61M 16/122 128/207.18 |
| 8,776,794 B2 | 7/2014 | Bathe et al. | |
| 8,776,795 B2 | 7/2014 | Bathe et al. | |
| 8,790,715 B2 | 7/2014 | Montgomery et al. | |
| 8,795,222 B2 | 8/2014 | Stenzler et al. | |
| 8,795,741 B2 | 8/2014 | Baldassarre | |
| 8,821,828 B2 | 9/2014 | Hilbig et al. | |
| 8,846,112 B2 | 9/2014 | Baldassarre | |
| 9,095,534 B2 | 8/2015 | Stenzler et al. | |
| 9,265,911 B2 | 2/2016 | Bathe et al. | |
| 9,279,794 B2 | 3/2016 | Tolmie et al. | |
| 9,295,802 B2 | 3/2016 | Bathe et al. | |
| 9,408,993 B2 | 8/2016 | Bathe et al. | |
| 9,573,110 B2 | 2/2017 | Montgomery et al. | |
| 9,770,570 B2 | 9/2017 | Schnitman et al. | |
| 9,795,756 B2* | 10/2017 | Flanagan | A61M 16/0677 |
| 9,982,354 B2 | 5/2018 | Kim | |
| 2001/0031230 A1 | 10/2001 | Castor et al. | |
| 2004/0019274 A1 | 1/2004 | Galloway, Jr. et al. | |
| 2004/0028753 A1 | 2/2004 | Hedenstierna et al. | |
| 2004/0031248 A1 | 2/2004 | Lindsey | |
| 2004/0181149 A1 | 9/2004 | Langlotz et al. | |
| 2005/0172971 A1 | 8/2005 | Kolobow et al. | |
| 2005/0218007 A1 | 10/2005 | Pekshev et al. | |
| 2005/0263150 A1 | 12/2005 | Chathampally et al. | |
| 2005/0281465 A1 | 12/2005 | Marquart et al. | |
| 2006/0025700 A1 | 2/2006 | Fallik | |
| 2006/0172018 A1 | 8/2006 | Fine et al. | |
| 2006/0276844 A1 | 12/2006 | Alon et al. | |

(56) References Cited

U.S. PATENT DOCUMENTS

| | | |
|---|---|---|
| 2007/0151561 A1 | 7/2007 | Laurila |
| 2007/0190184 A1 | 8/2007 | Montgomery et al. |
| 2008/0017030 A1 | 1/2008 | Fleck |
| 2008/0078382 A1 | 4/2008 | LeMahieu et al. |
| 2008/0135044 A1 | 6/2008 | Freitag et al. |
| 2008/0202509 A1 | 8/2008 | Dillon et al. |
| 2010/0189808 A1 | 7/2010 | Gupta et al. |
| 2010/0275911 A1 | 11/2010 | Arlow et al. |
| 2012/0279500 A1 | 11/2012 | Singvogel et al. |
| 2012/0296265 A1 | 11/2012 | Dobrynin et al. |
| 2013/0123801 A1 | 5/2013 | Umasuthan et al. |
| 2013/0150863 A1 | 6/2013 | Baumgartner |
| 2014/0031668 A1 | 1/2014 | Mobasser et al. |
| 2014/0158121 A1 | 6/2014 | Flanagan et al. |
| 2014/0216452 A1 | 8/2014 | Miller et al. |
| 2014/0251787 A1 | 9/2014 | Montgomery et al. |
| 2014/0363525 A1 | 12/2014 | Montgomery et al. |
| 2015/0000659 A1 | 1/2015 | Martin |
| 2015/0004248 A1 | 1/2015 | Morfill et al. |
| 2015/0034084 A1 | 2/2015 | Av-Gay et al. |
| 2015/0044305 A1 | 2/2015 | Av-Gay et al. |
| 2015/0072023 A1 | 3/2015 | Greenberg et al. |
| 2015/0090261 A1 | 4/2015 | Crosbie |
| 2015/0174158 A1 | 6/2015 | Av-Gay et al. |
| 2015/0272988 A1 | 10/2015 | Av-Gay et al. |
| 2016/0022731 A1 | 1/2016 | Av-Gay et al. |
| 2016/0030699 A1 | 2/2016 | Zapol et al. |
| 2016/0038710 A1 | 2/2016 | Zapol et al. |
| 2016/0183841 A1 | 6/2016 | Duindam et al. |
| 2016/0191887 A1 | 6/2016 | Casas |
| 2016/0228670 A1 | 8/2016 | Av-Gay et al. |
| 2016/0243328 A1 | 8/2016 | Tolmie et al. |
| 2016/0324580 A1 | 11/2016 | Esterberg |
| 2016/0367775 A1 | 12/2016 | Tolmie et al. |
| 2017/0014571 A1 | 1/2017 | Deem et al. |
| 2017/0014591 A1 | 1/2017 | Tolmie et al. |
| 2017/0014592 A1 | 1/2017 | Tolmie et al. |
| 2017/0021124 A1 | 1/2017 | Tolmie et al. |
| 2017/0065631 A1 | 3/2017 | Av-Gay et al. |
| 2017/0143758 A1 | 5/2017 | Greenberg et al. |
| 2017/0239289 A1 | 8/2017 | Av-Gay et al. |
| 2018/0049622 A1 | 2/2018 | Ryan et al. |
| 2018/0125883 A1 | 5/2018 | Av-Gay et al. |
| 2018/0133246 A1 | 5/2018 | Av-Gay et al. |

FOREIGN PATENT DOCUMENTS

| | | |
|---|---|---|
| CN | 101828432 A | 9/2010 |
| EP | 0621051 A2 | 10/1994 |
| EP | 1036758 A1 | 9/2000 |
| EP | 1854494 A1 | 11/2007 |
| EP | 2151554 A1 | 2/2010 |
| JP | H04132560 A | 5/1992 |
| JP | 2000102616 A | 4/2000 |
| JP | 2001517108 A | 10/2001 |
| JP | 2004065636 A | 3/2004 |
| JP | 2006273677 A | 10/2006 |
| WO | 9507610 A1 | 3/1995 |
| WO | 2004032719 A2 | 4/2004 |
| WO | 2011002606 A1 | 1/2011 |
| WO | 2012094008 A1 | 7/2012 |
| WO | 2013052548 A2 | 4/2013 |
| WO | 2013070712 A1 | 5/2013 |
| WO | 2013181179 A1 | 12/2013 |
| WO | 2014085719 A1 | 6/2014 |
| WO | 2014143842 A1 | 9/2014 |
| WO | 2015066278 A1 | 5/2015 |
| WO | 2015127085 A1 | 8/2015 |
| WO | 2016064863 A1 | 4/2016 |

OTHER PUBLICATIONS

Li, et al., Production of Medically Useful Nitric Monoxide Using AC Arc Discharge, Nitric Oxide, 2018, 73:89-95.

Mok, et al., Application of Positive Pulsed Corona Discharge to Removal of SO2 and NOx, Proceedings, ICESP VII, Sep. 20-25, 1998, Kyongju, Korea, 8 pages.

Namihira, et al., Production of Nitric Oxide Using a Pulsed Arc Discharge, IEEE Transactions on Plasma Science, 2002, 30(5):1993-1998.

PCT International Search Report, PCT/US2014/028439, dated Jul. 24, 2014.

PCT International Preliminary Report on Patentability, PCT/US2014/028439, dated Sep. 15, 2015.

PCT International Search Report, PCT/US2014/027986, dated Jul. 17, 2014.

PCT International Preliminary Report on Patentability, PCT/US2014/027986, dated Sep. 15, 2015.

PCT International Search Report and Written Opinion, PCT/US2015/056443, dated Jan. 6, 2016.

PCT International Search Report and Written Opinion, PCT/US2017/024331, dated Jun. 15, 2017.

\* cited by examiner

| FiO$_2$ | 0.21 | 0.21 |
|---|---|---|
| B | 100 | 100 |
| N | 70 | 70 |
| P | 140 | 140 |
| H | 10 | 17 |
| Continuous sparking | yes | yes |
| Flow rate (L/min) | 1 | 1 |
| [NO] (ppm) | 145-150 | 250 (maximum) |

FIG. 35

INSPIRATORY SYNTHESIS OF NITRIC OXIDE

CROSS-REFERENCE TO RELATED APPLICATIONS

The present application is a continuation of U.S. patent application Ser. No. 16/058,797 filed Aug. 8, 2018, which is a continuation of U.S. patent application Ser. No. 14/777,072 filed Sep. 15, 2015, which represents the national stage entry of PCT International Application No. PCT/US2014/028439 filed Mar. 14, 2014, which claims priority to U.S. Patent Application Ser. No. 61/789,161 filed Mar. 15, 2013, and U.S. Provisional Application Ser. No. 61/792,473, filed Mar. 15, 2013, which are hereby incorporated by reference in their entirety for all purposes.

TECHNICAL FIELD

This invention related to synthesis of nitric oxide triggered by inspiratory flow.

BACKGROUND

Nitric oxide (NO) is crucial to many biological systems, and is known to mediate the control of blood pressure, help the immune system kill invading parasites that enter cells, inhibit division of cancer cells, transmit signals between brain cells, and contribute to the large scale death of brain cells that can debilitate people with strokes or Huntington's disease. Nitric oxide also mediates relaxation of smooth muscle present, for example, in the walls of the blood vessels, bronchi, gastrointestinal tract, and urogenital tract. Administration of nitric oxide gas to the lung by inhalation has been shown to produce localized smooth muscle relaxation to treat bronchial constriction and pulmonary hypertension, pneumonia, etc. in adults and children without systemic side effects.

Inhaled nitric oxide is a potent local pulmonary vasodilator and bronchodilator that improves the matching of ventilation with perfusion, thereby increasing the injured lungs oxygen transport efficiency and raising the arterial oxygen tension. Nitric oxide combines a rapid onset of action occurring within seconds with the absence of systemic vasodilatory effects. Once inhaled, it diffuses through the pulmonary vasculature into the bloodstream, where it is rapidly inactivated by combination with hemoglobin. Therefore, the bronchodilator effects of inhaled nitric oxide are limited to the airway and the vasodilatory effects of inhaled nitric oxide are limited to the pulmonary vasculature. The ability of nitric oxide to dilate pulmonary vessels selectively provides therapeutic advantages in the treatment of acute and chronic pulmonary hypertension.

U.S. Pat. No. 5,396,882 to Zapol, which is incorporated by reference herein, describes electric generation of nitric oxide (NO) from air at ambient pressure for medical purposes. As described in U.S. Pat. No. 5,396,882, an air input port of the system is used for continuously introducing air into the electric arc chamber. Unwanted by-products formed during the production of NO (e.g., nitrogen dioxide ($NO_2$) and ozone ($O_3$)) are absorbed, for example, by a scavenger or catalytic converter before the electrically generated NO is used for medical purposes.

NO oxidizes in an oxygen-containing atmosphere to form $NO_2$. $NO_2$ is a toxic by-product which forms nitric acid when dissolved in airway secretions or cells. Generating NO with low levels of $NO_2$ is often desirable.

SUMMARY

In some aspects, a method includes collecting information related to one or more triggering events associated with a respiratory system. The method also includes determining one or more control parameters based on the collected information. The method also includes initiating a series of electric arcs to generate nitric oxide based on the determined control parameters.

Embodiments can include one or more of the following.

The triggering event can be a reduction of temperature due to an inspiration of gas.

The triggering event can be a flow of gas.

The information related to one or more triggering events can include one or more of an onset time of an inspiration, a tidal volume of an inspiration, a temperature of an inspired gas, and a concentration of oxygen in a reactant gas.

The series of electric arcs can be produced when the triggering event occurs.

The series of electric arcs can be produced a pre-defined amount of time before the triggering event occurs.

A pulse train can initiate the series of electric arcs, and the pulse train can include pulse groups having pulses with different pulse widths.

The pulse width of initial pulses in one of the pulse groups can be wider than other pulses in the pulse group.

The series of electric arcs can generate a reduced level of nitrogen dioxide or ozone.

The reduced level of nitrogen dioxide can have a concentration that is less than 20%, 10%, 6%, or 5% of a concentration of the generated nitric oxide.

The respiratory system can include a trachea.

The respiratory system can include one or both of a tracheostomy tube and an endotracheal tube.

The respiratory system can include a patient wearable mask.

In some additional aspects, an apparatus includes a respiration sensor for collecting information related to one or more triggering events associated with a respiratory system. The apparatus also includes an oxygen sensor for collecting information related to a concentration of oxygen in a gas. The apparatus also includes a controller for determining one or more control parameters based on the collected information. The apparatus also includes electrodes for initiating a series of electric arcs to generate nitric oxide based on the determined control parameters.

Embodiments can include one or more of the following.

The triggering event can be a reduction of temperature due to an inspiration of gas.

The triggering event can be a flow of gas past the respiration sensor.

The information related to one or more triggering events can include one or more of an onset time of an inspiration, a tidal volume of an inspiration, a temperature of an inspired gas, and a concentration of oxygen in a reactant gas.

The electrodes can produce the series of electric arcs when the triggering event occurs.

The electrodes can produce the series of electric arcs a pre-defined amount of time before the triggering event occurs.

A pulse train can initiate the series of electric arcs, and the pulse train can include pulse groups having pulses with different pulse widths.

The pulse width of initial pulses in one of the pulse groups can be wider than other pulses in the pulse group.

The series of electric arcs can generate a reduced level of nitrogen dioxide or ozone.

The reduced level of nitrogen dioxide can have a concentration that is less than 20%, 10%, 6%, or 5% of a concentration of the generated nitric oxide.

The respiratory system can include a trachea.

The respiratory system can include one or both of a tracheostomy tube and an endotracheal tube.

The respiratory system can include a patient wearable mask.

The patient wearable mask can include one or more valves for separating an inspiratory gas flow from an expiratory gas flow.

The sensor or the electrodes can be configured to be positioned in a trachea.

The electrodes can include a noble metal.

The electrodes can include iridium.

The electrodes can include nickel.

In some additional aspects, a system for generating nitric oxide includes an apparatus positioned in a trachea of a mammal. The apparatus includes a respiration sensor for collecting information related to one or more triggering events associated with the trachea. The apparatus also includes an oxygen sensor for collecting information related to a concentration of oxygen in a gas. One or more pairs of electrodes are included in the apparatus for initiating a series of electric arcs to generate nitric oxide. The system for generating nitric oxide also includes a controller for determining one or more control parameters based on the information collected by the respiration sensor and the oxygen sensor, wherein the series of electric arcs is initiated based on the control parameters determined by the controller.

Embodiments can include one or more of the following.

The triggering event can be a reduction of temperature due to an inspiration of gas.

The triggering event can be a flow of gas past the respiration sensor.

The information related to one or more triggering events can include one or more of an onset time of an inspiration, a tidal volume of an inspiration, a temperature of an inspired gas, and a concentration of oxygen in a reactant gas.

The electrodes can produce the series of electric arcs when the triggering event occurs.

The electrodes can produce the series of electric arcs a pre-defined amount of time before the triggering event occurs.

A pulse train can initiate the series of electric arcs, and the pulse train can include pulse groups having pulses with different pulse widths.

The pulse width of initial pulses in one of the pulse groups can be wider than other pulses in the pulse group.

The series of electric arcs can generate a reduced level of nitrogen dioxide or ozone.

The reduced level of nitrogen dioxide can have a concentration that is less than 20%, 10%, 6%, or 5% of a concentration of the generated nitric oxide.

The electrodes can include a noble metal.

The electrodes can include iridium.

The electrodes can include nickel.

In some additional aspects, an apparatus implantable in the intercartilaginous rings in the neck includes a respiration sensor for collecting information related to one or more triggering events associated with a respiratory system. The apparatus also includes an oxygen sensor for collecting information related to a concentration of oxygen in a gas.

The apparatus also includes a controller for determining one or more control parameters based on the collected information. One or more pairs of electrodes are included in the apparatus and reside inside a spark chamber, the electrodes for initiating a series of electric arcs to generate nitric oxide based on the determined control parameters, wherein the spark chamber is separated from an external environment by a membrane that is permeable to nitric oxide and impermeable to nitrogen dioxide and ozone.

Embodiments can include one or more of the following.

The apparatus can also include a sweeping device for removing mucus from the membrane.

In some additional aspects, an apparatus implantable in the trachea of a mammal using the Seldinger technique includes a respiration sensor for collecting information related to one or more triggering events associated with a respiratory system. The apparatus also includes an oxygen sensor for collecting information related to a concentration of oxygen in a gas. The apparatus also includes a controller for determining one or more control parameters based on the collected information. One or more pairs of electrodes are included in the apparatus for initiating a series of electric arcs to generate nitric oxide based on the determined control parameters.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 35 shows NO production under a constant reactant gas flow rate using a modified mini spark plug with a circuit gap.

Like reference symbols in the various drawings indicate like elements.

DETAILED DESCRIPTION

Figure 1:
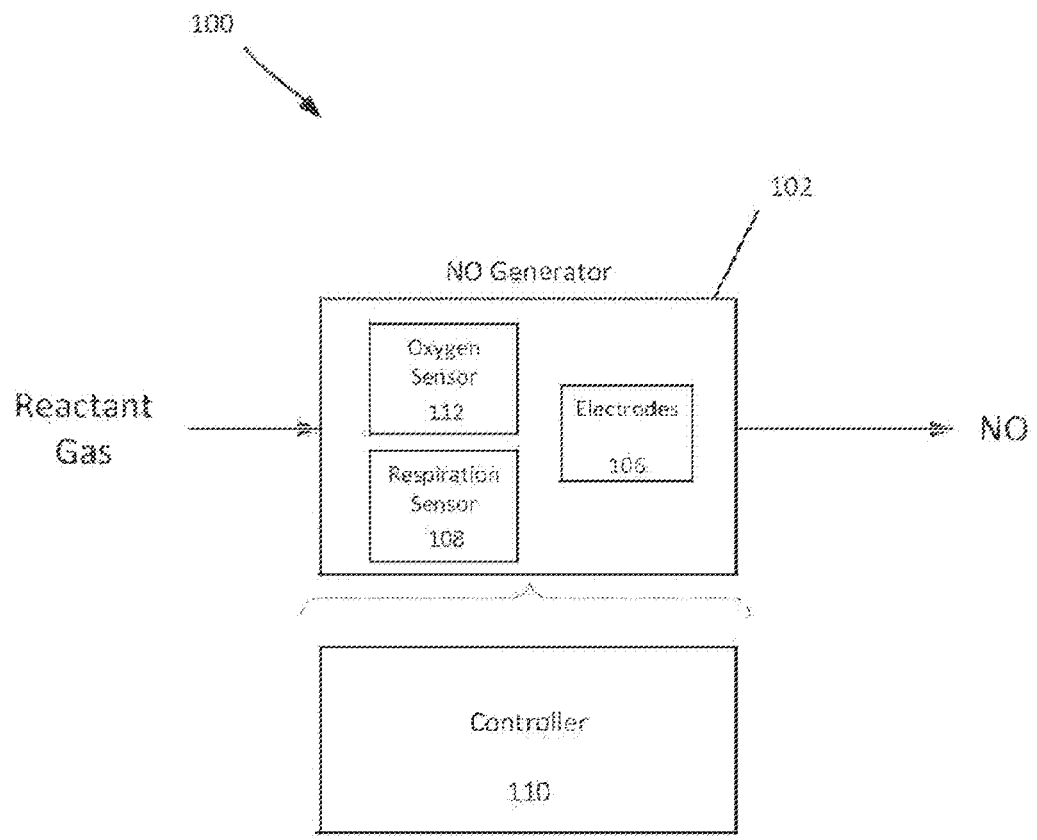
FIG. 1 is a block diagram of a system for producing NO.

As described herein, electrical synthesis of nitric oxide is initiated upon (or before) inspiration to provide in-situ, on-demand production of nitric oxide for therapeutic use. FIG. 1 shows an example of a system 100 for producing NO in a respiratory system. In some examples, a respiratory system includes the trachea of a mammal, a respiratory mask, nasal prongs, a ventilator, or an anesthesia machine, to name a few. A reactant gas (e.g., air, or a 20-90% oxygen mixture in nitrogen) enters an NO generator 102, and a product gas (including NO) exits the NO generator 102. The NO generator 102 includes electrodes 106, a respiration sensor 108, and a controller 110. If the reactant gas is a gas other than air, the NO generator 102 can include an oxygen sensor 112. The oxygen sensor 112 can be an electrode configured to detect the concentration of oxygen in the reactant gas. The electrodes 106 generate sparks in the presence of the reactant gas to produce NO 104, as described herein.

Figure 2A:
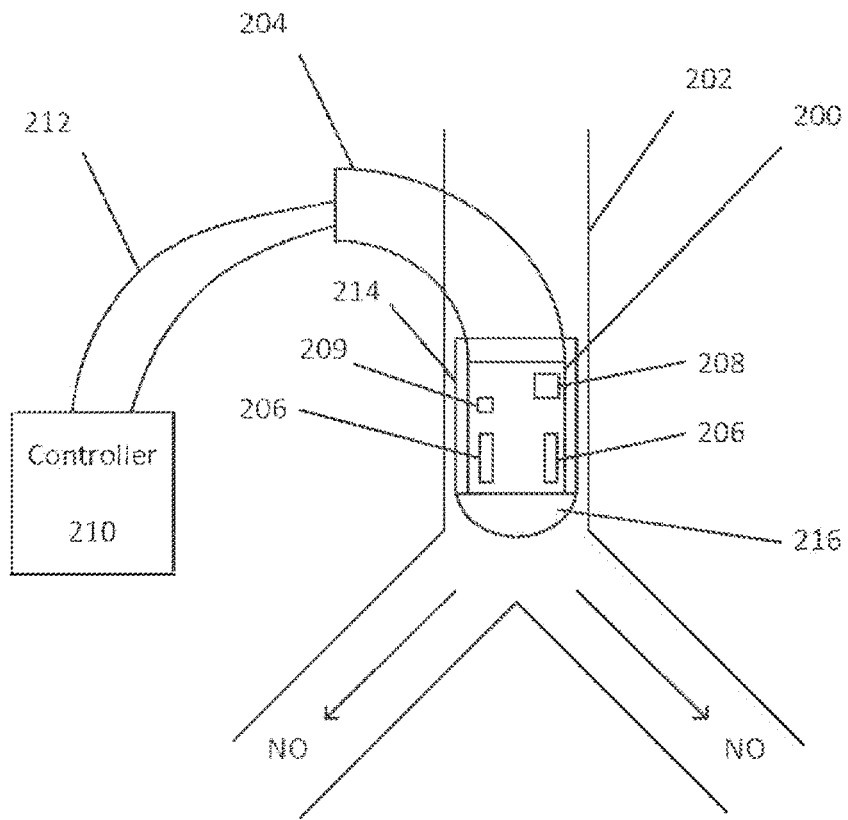
FIG. 2A shows an example of an NO generator.

In some embodiments, the NO generator 102 is portable and wearable. For example, FIG. 2A shows an example of an NO generator 200 for producing NO that can reside within the trachea of a mammal. The device can be placed in the larynx with a fiber bronchoscope, and anchored to the tracheal wall. FIG. 2A depicts a cross-sectional view of a trachea 202 with tracheostomy or endotracheal tube 204 positioned in the trachea 202. The NO generator 200 is coupled to the tracheostomy or endotracheal tube 204. The NO generator 200 includes electrodes 206 and respiration sensor 208. In some examples, the NO generator 200 includes an oxygen sensor 209. The NO generator 200 may include a controller 210 that is coupled to the electrodes 206, the respiration sensor 208, and the oxygen sensor 209. In some examples, the controller 210 is separate from the NO generator 200. The NO generator 200 may include more than one respiration sensor 208.

In some examples, the electrodes 206 can be duplicated for safety purposes to provide a spare. The electrodes 206 can be doubled or tripled for increased power and NO production, e.g., with large tidal volumes.

The electrodes, power feed, and sensor wires can be embedded in the wall of the tracheostomy or endotracheal tube 204. The electrodes may be positioned within the tube, or placed in a small enclosure or well in the wall of the tube. The enclosure can be a spark reaction chamber that is covered by a microporous membrane to shield the electrodes from mucus or respiratory secretions. The membrane can also be a semipermeable membrane (permselective) such as DMPS that passes NO without passing water vapor. The membrane can be any membrane for passing NO without passing $NO_2$. A small internal scraper can be placed over the membrane to remove adherent mucus or respiratory secretions that might prevent diffusion of the NO into the lumen. The scraper may be controlled externally.

The controller 210 may be internal to or external from the user. For example, the controller 210 may be coupled to a user (e.g., an arm band or belt) or implanted subcutaneously in the user. Electrodes 206, respiration sensor 208, and leads 212 may be embedded in the wall of tracheostomy or endotracheal tube 204 or positioned inside or affixed to an exterior of the tracheostomy or endotracheal tube 204. Leads 212 may be insulated with an inert material. The leads 212 can be coupled to the electrodes 206 and the respiration sensor 208. In some examples, the leads 212 can be separately placed via a needle puncture between the cartilaginous tracheal rings (Seldinger technique). Respiration sensor 208 may be, for example, one or more of a pressure sensor, a temperature sensor, a gas velocity sensor (e.g., a heated wire anemometer), a tidal volume sensor, an abdominal or thoracic plethysmographic band (Respitrace™) or the like. In some cases, electrodes 206 and/or respiration sensor 208 are at least partially covered by a shield 214. Shield 214 may be positioned proximate to a balloon 216 of the tracheostomy or endotracheal tube 204, designed to insulate the airway from electrical shock and to keep electrodes 206 and respiration sensor 208 clean.

In some cases, a sweeping device, brush, scraper, sander or other cleaning device, automated or not, is coupled to shield 214. Shield 214 may also include a filter, e.g., a microporous membrane such as polytetrafluoroethylene, or a diffusible but permselective membrane such as PDMB, or polymethylpentene (PMP), so that by-products generated at electrodes 206 (such as $NO_2$ and $O_3$) do not pass into the airway. The filter or membrane may also keep particulate matter or vapor in the airway such as humidity and mucus from contacting the electrodes 206 and respiration sensor 208.

Figure 2B:
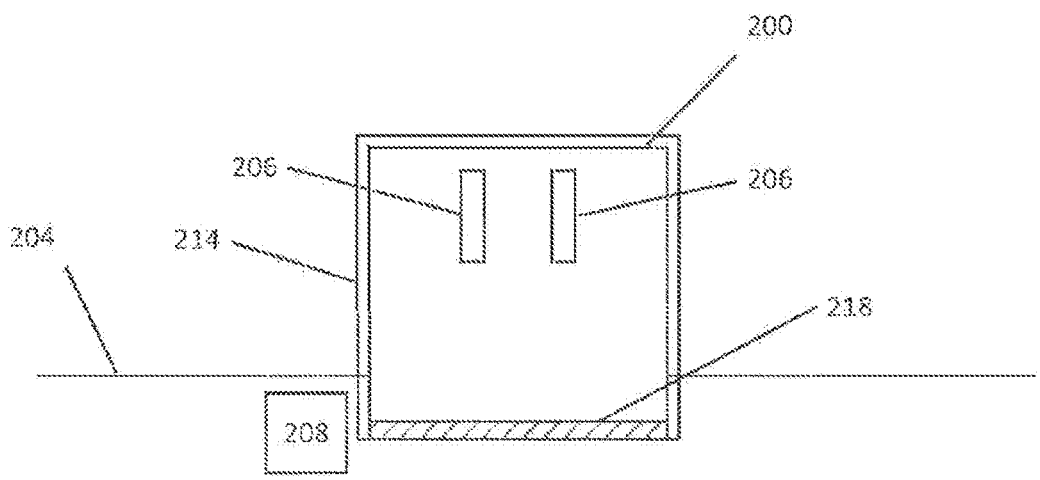
FIG. 2B shows an example of an NO generator.

FIG. 2B shows an example of an alternative arrangement for the NO generator 200 coupled to the tracheostomy or endotracheal tube 204. In this example, the shield 214 includes a permselective membrane 218. The area where the electrodes 206 reside (e.g., inside the NO generator 200) is referred to as a spark chamber. The permselective membrane 218 can be approximately 10-50 microns thick, and may be affixed to a support mesh. The permselective membrane 218 can allow NO to pass from the NO generator 200 (e.g., the spark chamber) to the airway while preventing $NO_2$ and $O_3$ from passing from the NO generator 200 (e.g., the spark chamber) to the airway. The permselective membrane 218 can also prevent water vapor from passing from the airway to the NO generator 200. In some examples, the permselective membrane 218 can be a microporous membrane. In this example, the respiration sensor 208 resides in the tracheostomy or endotracheal tube 204. However, the respiration sensor 208 can also reside in the NO generator 200, as described with reference to FIG. 2A. In some examples, a sweeping device is coupled to the NO generator 200. The sweeping device is configured to remove mucus from the permselective membrane 218. The sweeping device may be automated.

Figure 2C:
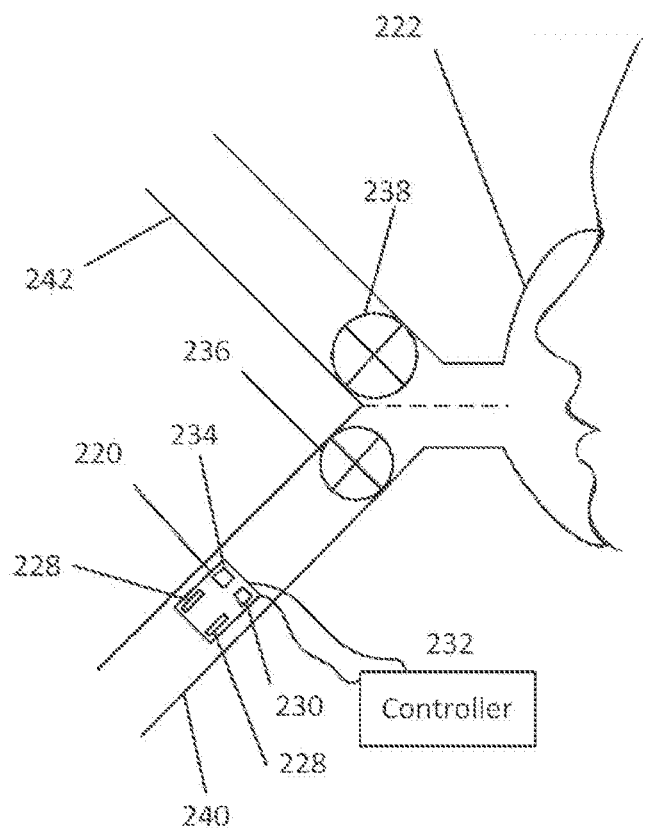
FIG. 2C shows an example of an NO generator.

FIG. 2C shows an example of an NO generator 220 for producing NO that is attached to a mask 222 that can be worn by a patient. Portions of the NO generator 220 can be placed within a nasal cavity, for example in the vestibule behind the naris, as in the NO generator 200 of FIG. 2A. The mask 222 can be part of a respiratory system. The mask 222 is configured to be positioned over a user's face, with electrodes 228 and respiration sensor 230 coupled to the mask 222 and positioned proximate the nasal opening of a user. In some examples, the NO generator 220 includes an oxygen sensor 234. The NO generator 220 may reside in an inspiratory line 240 that feeds into the mask 222. The mask 222 can include one or more valves (e.g., inspiratory valve 236 and expiratory valve 238) for separating inspiratory gas flow from the inspiratory line 240 from expiratory gas flow through the expiratory line 242. A controller 232 may be coupled to the NO generator 220. The controller 232 may be coupled to mask 222 or to the user. In some examples, the electrodes 228 and respiration sensor 230 can be positioned in a nostril of the user. The NO generator 220 functions as described above with respect to the NO generator 200 of FIG. 2A. The entry to the mask 222 may have one or more valves, an inspiration line, and an expiration line. The NO generator 220 may be placed in the inspiration line.

Figure 2D:
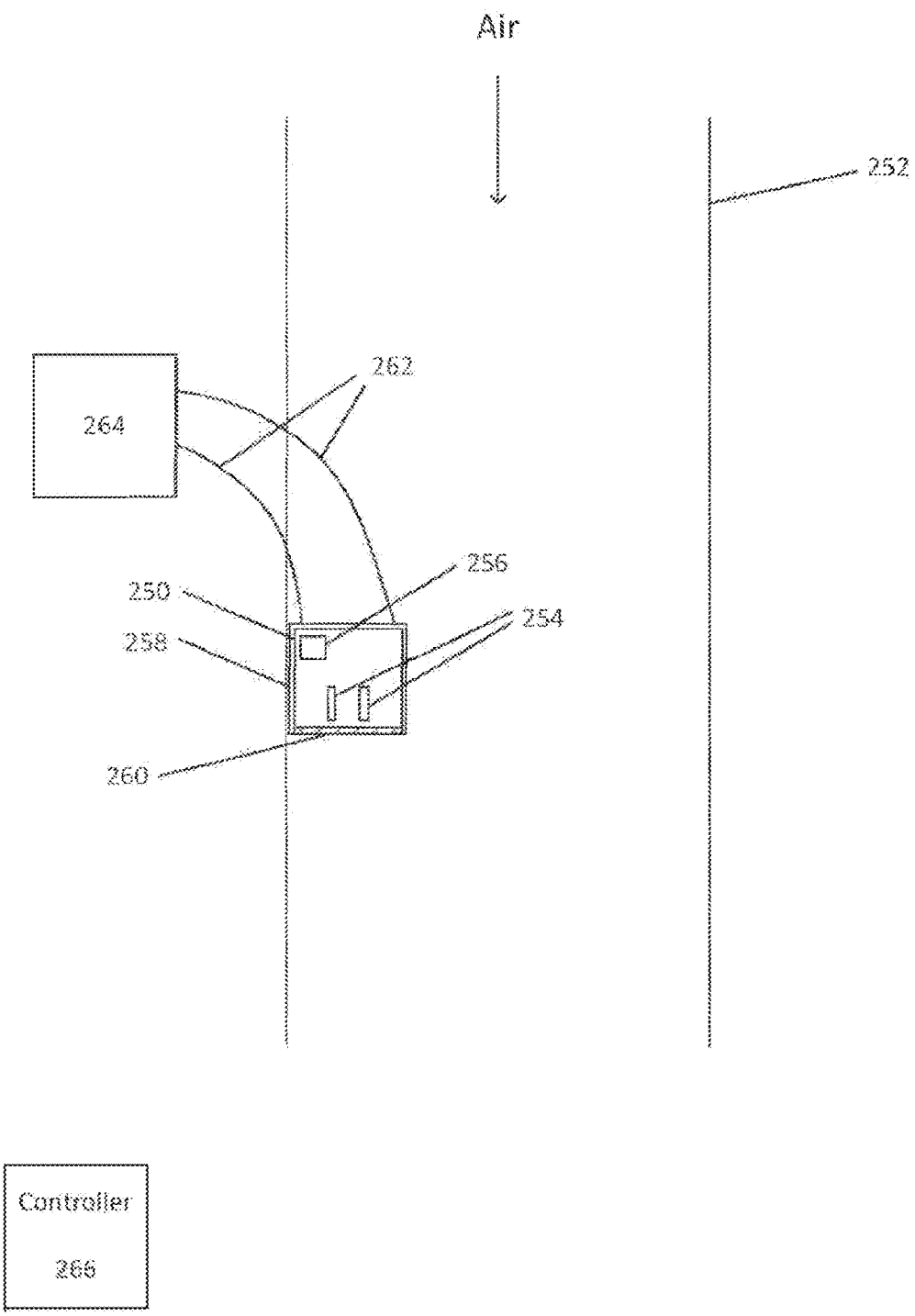
FIG. 2D shows an example of an NO generator.

FIG. 2D shows an example of an NO generator 250 for producing NO that can reside within a trachea 252. In some examples, the NO generator 250 is small enough to be implanted using the Seldinger technique. The NO generator 250 includes electrodes 254 and a respiration sensor 256 (e.g., including a thermistor). The NO generator 250 may be covered by a shield 258 to insulate the airway from electrical shock and to keep the electrodes 254 and respiration sensor 256 clean. The NO generator may also include a membrane 260. The membrane 260 may be a permselective membrane that can allow NO to pass from the NO generator 250 to the airway while preventing $NO_2$ and $O_3$ from passing from the NO generator 250 to the airway. The membrane 260 can also prevent water vapor from passing from the airway to the NO generator 250. Wires 262 can connect a power source 264 to the NO generator 250. The wires 262 can be insulated to protect tissue from electric shock. A controller (e.g., controller 266) may be configured to communicate with the NO generator 266. The controller 266 may be configured to wirelessly communicate with the NO generator 250. In some examples, the NO generator 250 includes the controller 266, and the controller 266 resides within the trachea 252.

Referring back to FIG. 2A, the NO generator 200 operates as described herein to generate NO in the airway of a mammal based on a triggering event (e.g., volume and timing of gas flow, change in inspired gas temperature, or change in pressure), as detected by respiration sensor 208 in some examples. The controller 210, operatively coupled to respiration sensor 208, coordinates triggering of a voltage source in the controller 210 to deliver a series of electrical pulses to electrodes 206, thereby generating NO in the airway of the mammal during inspiration. The controller 210 can determine one or more control parameters based on information that is collected from the respiration sensor 208 (e.g., information related to one or more triggering events). The controller 210 may be configured to initiate a series of sparks and to control parameters such as spark duration, spark frequency, and the like to generate the needed amount of NO and minimal amount of $NO_2$. In some examples, the voltage source in the controller 210 can be a primary cell battery, a rechargeable battery, or a piezoelectric generator.

The controller 210 can determine one or more control parameters based on information received from an oxygen sensor (e.g., oxygen sensor 112 of FIG. 1). For example, the determined control parameters can be based on the concentration of oxygen in the reactant gas.

In some examples, the respiration sensor 208 is configured to measure the tidal volume of inspired gas. The controller 210 can determine one or more control parameters based on the inspired gas volume measurements. For example, the control parameters can be based on an actual or expected volume of an inspiration.

Adult humans normally breathe from 10-20 times per minute, each breath having a duration of 3-6 seconds. Typically, about one half to one third of the breath duration is inspiration. On average, each breath has a tidal volume of about 500 ml. In children, each breath typically has less volume, but breathing occurs at a higher rate.

The expected volume of an inspiration can be calculated using previous tidal volume measurements. For example, the controller 210 may determine that the expected tidal volume of a subsequent inspiration is going to be the same as the tidal volume measurement for the most recent inspiration. The controller 210 can also average the tidal volumes of several prior inspirations to determine the expected tidal volume of a subsequent inspiration. In some instances, mechanical ventilation is applied via a mask to support ventilation. In those cases, the inspiratory volume and timing of inspiration can be fed to the controller from the ventilator device.

Figure 3:
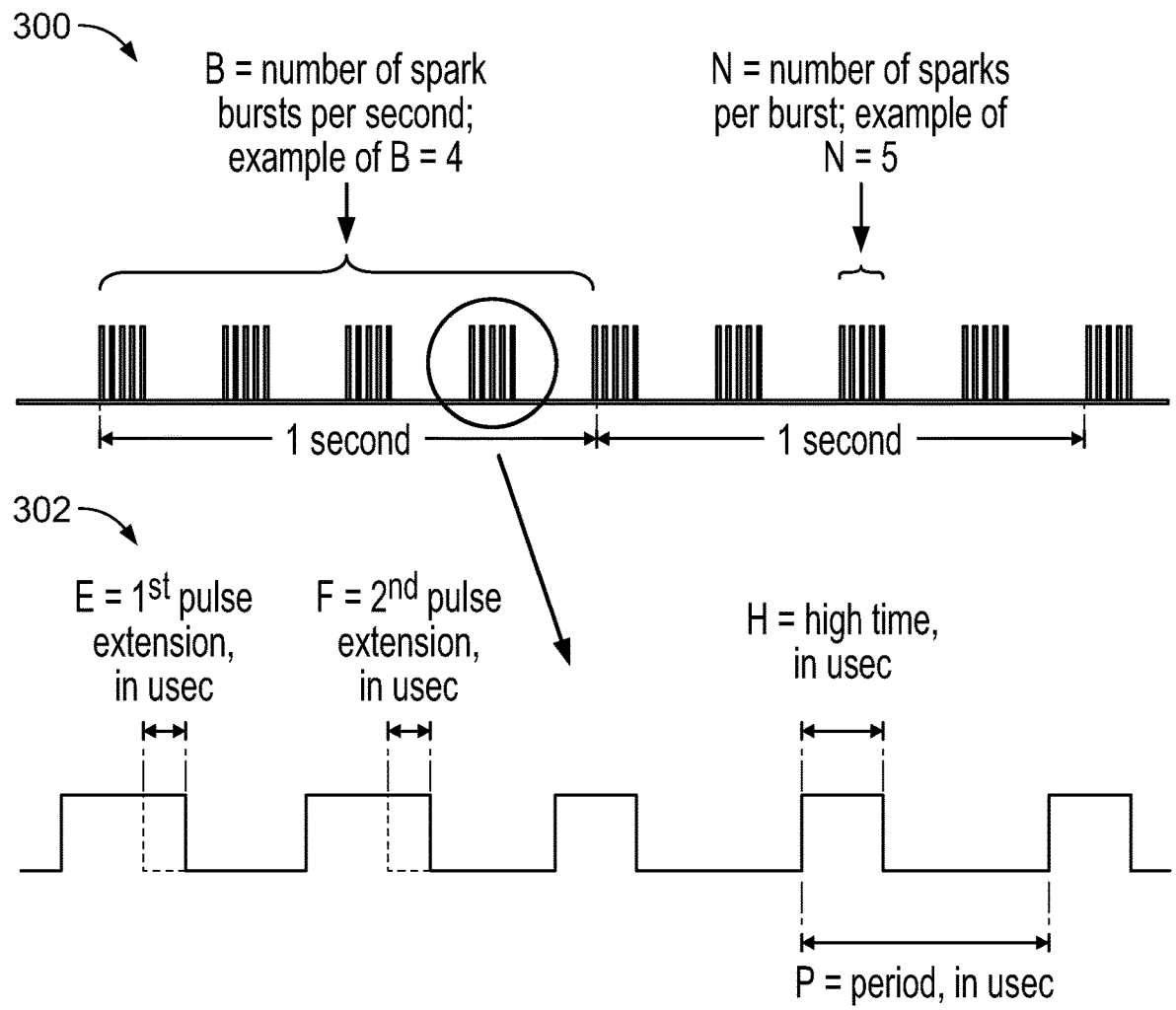
FIG. 3 depicts a representation of a pulse train and a pulse group.

FIG. 3 shows a representation of a pulse train 300 that is triggered by the controller 210. The controller 210 can determine one or more control parameters to create a pulse train. FIG. 3 also shows zoomed in view of one of the pulse groups 302 of the pulse train 302. Electrical pulses are delivered to the electrodes 206, and the electrodes 206 generate a series of sparks (sometimes referred to as electric arcs). The timing of the pulses (and of the resulting sparks) is controlled by the controller 210, and can be optimized to produce the needed amount of NO while producing minimal $NO_2$ and $O_3$. Multiple sparks make up a pulse group, and multiple pulse groups make up the pulse train. Thus, the pulse train 302 initiates the series of electric arcs.

Variables B and N control the overall energy that is created by the electrodes 206. Variable N sets the number of sparks per pulse group, and variable B sets the number of pulse groups per second. The values for B and N influence the amount of NO, $NO_2$, and $O_3$ that is created. The values for B and N also influence how much heat is produced by the electrodes 206. Larger values of either B or N create more NO and cause the electrodes 206 to produce more heat.

Variables E, F, H, and P control the timing of the sparks produced in each pulse group. Variable H is the high time of a pulse (e.g., the amount of time the voltage source of the controller 210 is activated for each electrical pulse). The high time is sometimes referred to as the pulse width. P is the amount of time between pulses. Thus, P minus H represents a period of time when no pulses occur (e.g., the voltage source of the controller 210 is not active). Larger values of H and smaller values of P result in the electrodes 206 producing more energy. When the electrodes 206 create a spark, plasma is established. The temperature of the plasma is proportional to the amount of energy produced by the electrodes 206.

The chemical reactions that cause NO and $NO_2$ to be produced are a function of plasma temperature. That is, higher plasma temperatures result in more NO and $NO_2$ being produced. However, the relative proportions of the produced NO and $NO_2$ vary across different plasma temperatures. In some examples, the sparks generated by the first two pulses in a pulse group establish the plasma. The first two sparks can have a high time that is longer than the sparks produced by the rest of the pulses in the pulse group. The amount of time that the first two pulses are extended is represented by variables E and F, respectively. Sparks generated by pulses beyond the first two pulses require less energy to maintain the plasma, so the high time of subsequent pulses (represented by variable H) can be shorter to prevent the plasma temperature from getting too high. For instance, while a relatively high plasma temperature may result in more NO, $NO_2$, and $O_3$ being produced, the relatively high plasma temperature may not be ideal for producing the desired proportions of NO and $NO_2$.

Figure 8:
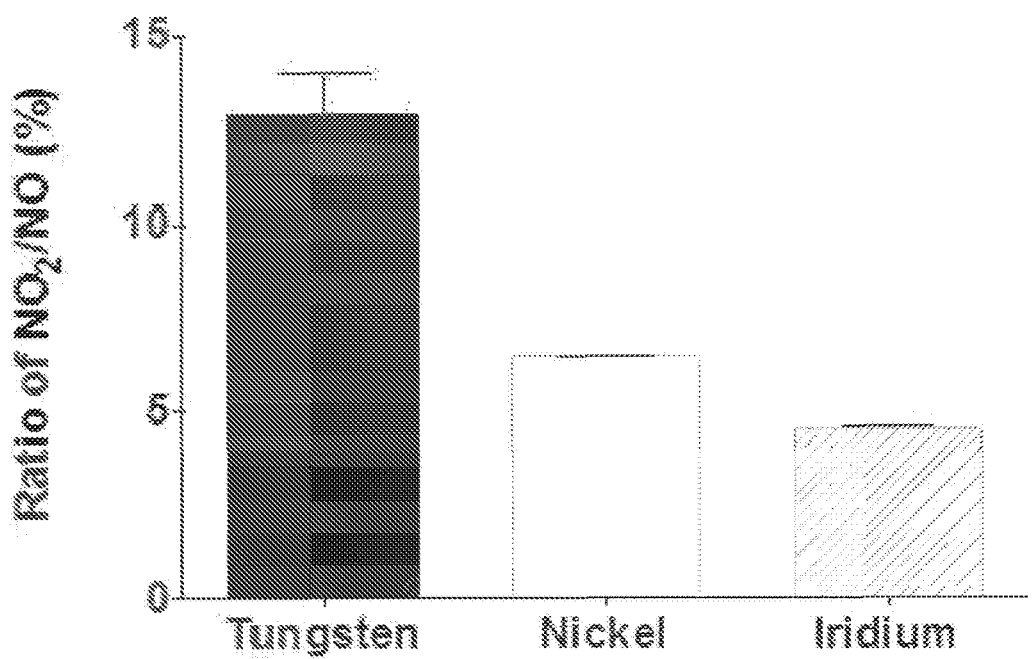
FIG. 8 shows NO and $NO_2$ concentrations using various electrode materials.

Many factors can affect the amount and proportions of NO, $NO_2$, and $O_3$ that is produced. For example, the material of the electrodes 206 plays a major role in determining how much energy is needed to generate a particular spark. Electrodes that include a noble metal may produce a low ratio of $NO_2/NO$. In some examples, tungsten electrodes produce a relatively high ratio of $NO_2/NO$, nickel electrodes produced a lower ratio of $NO_2/NO$, and iridium electrodes produce an even lower ratio of $NO_2/NO$, as shown in FIG. 8.

Each spark that is generated creates a particular amount of NO. The NO is diluted in the volume of gas that is inspired. To ensure the concentration of NO in the inspired gas is at an expected and sufficient level to produce the desired physiological effect, the controller 210 receives information related to the tidal volume of inspired gas from the respiration sensor 208 to determine control parameters for maintaining an appropriate NO concentration.

Implementations of the controller 210 can include digital electronic circuitry, or computer software, firmware, or hardware, including the structures disclosed in this specification and their structural equivalents, or combinations of one or more of them. For example, the controller 210 can be a microprocessor based controller (or control system) as well as an electro-mechanical based controller (or control system). Instructions and/or logic in the controller 210 can be implemented as one or more computer programs, i.e., one or more modules of computer program instructions, encoded on computer storage medium for execution by, or to control the operation of, data processing apparatus. Alternatively or in addition, the program instructions can be encoded on an artificially generated propagated non-transitory signal, e.g., a machine-generated electrical, optical, or electromagnetic signal that is generated to encode information for transmission to suitable receiver apparatus for execution by a data processing apparatus.

The controller 210 can include clients and servers and/or master and slave controllers. A client and server are generally remote from each other and typically interact through a communication network. The relationship of client and server arises by virtue of computer programs running on the respective computers and having a client-server relationship to each other. In some aspects, the controller 210 represents a main controller (e.g., master) communicably coupled through communication elements (e.g., wired or wireless) with each of the components of the NO generator 200.

The controller 210 may be configured to communicate with the NO generator 200 wirelessly (e.g., via Bluetooth). The controller 210 can also be configured to communicate with external devices (e.g., a computer, tablet, smart phone, or the like). The external devices can then be used to perform functions of the controller 210 or to aid the controller 210 in performing functions.

In some examples, the controller 210 can disable certain components of the NO generator 200 during, before or after a series of sparks is generated. In some examples, the controller 210 can also include features to: i) detect and cease unintended sparks; ii) confirm that a series of sparks is safe before triggering the series of sparks; iii) verify that timing values are checked against back-up copies of timing values after every series of sparks is generated to detect timing variable corruption; and iv) determine whether back-up copies of timing variables are corrupt.

In some examples, the NO generator 200 can be positioned or included with nasal tubes, endotracheal tubes, and the like. Electrodes 206 and respiration sensor 208 may be cleanable or replaceable. In some examples, the electrodes 106 and sensor 208 may be removed from the tracheostomy or endotracheal tube 204 and cleaned or replaced.

Sparking upon inspiration in the NO generator 200 tags the front of the inspired gas bolus with electrically synthesized fresh NO. In some examples, it is desirable to generate NO only at the start of inspiration. This minimizes the amount of freshly produced NO produced, reduces environmental pollution, and effectively delivers the NO most rapidly without dilution into terminal bronchi and alveolar gas where it can actively dilate the pulmonary blood vessels (the alveoli and distal airways). After a brief period of time, NO begins to oxidize into $NO_2$ which, when dissolved in water, forms nitric acid and nitrate salts. If NO is produced long before a user is ready to inhale it, the NO can be oxidized by the time of inspiration. The nitric acid and nitrate salts can cause damage to the components of the NO generator 200 as well as to the airways and lung tissue.

In some examples, to augment the dose, it may be desirable to generate NO at the end of exhalation and slightly prior to the start of an inspiration. This is sometimes referred to as pre-triggering. The controller 210 can initiate the series of electric arcs for a pre-defined amount of time before the triggering event occurs. Such pre-triggering may be necessary when there is a large volume of inspired gas or when a high concentration of inhaled NO is desired. The controller 210 can track the inspiratory timing and volume of inspired gas and use prior timings to predict the timing of a subsequent inspiration. The tracked information can be used to calculate a pre-defined amount of time that represents an estimate of when the next inspiration will occur. In some examples, the controller 210 can initiate the series of electric arcs approximately when the triggering event occurs (e.g., slightly before or slightly after the triggering event). Pre-triggering can be optimized to ultimately deliver greater NO concentrations in the inspired gas.

The spark can be triggered at the onset of inspiration in a number of ways. In some examples, the respiration sensor 208 detects an inspiration. The respiration sensor 208 can include a high speed response thermistor that is located near the electrodes 206 in the airway. The respiration sensor 208 can sense a change in temperature (inspired air is often slightly cooler than expired air). Thus the cool inspiratory gas can trigger a series of sparks. That is, an inspiration, or part of an inspiration, can be a triggering event. More specifically, a reduction of temperature due to an inspiration of air can be a triggering event.

Figure 4:
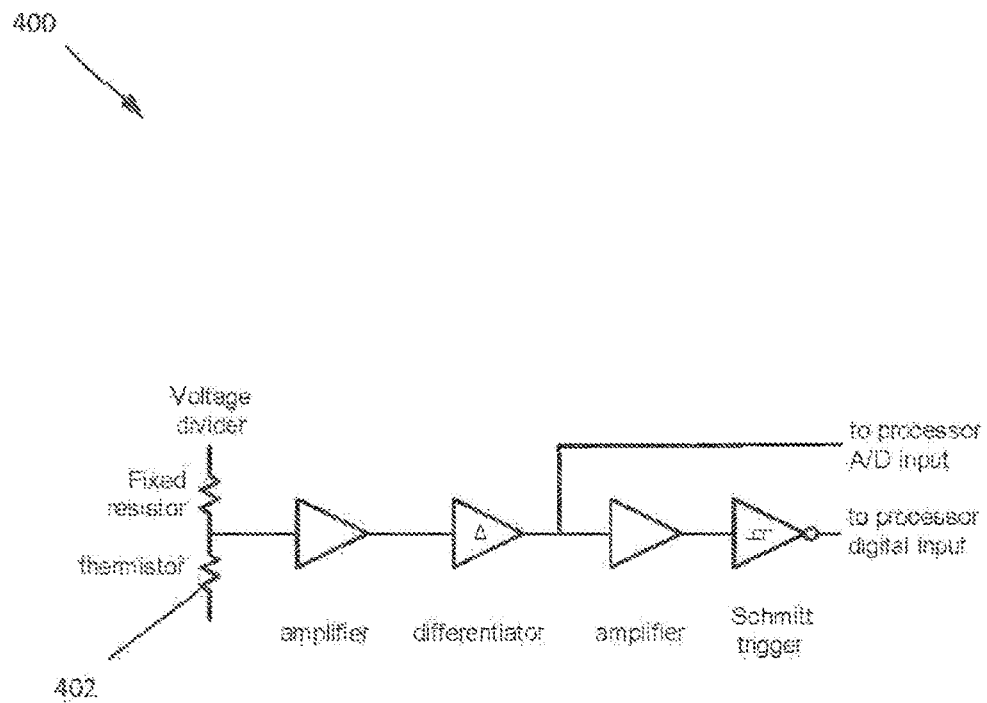
FIG. 4 is a circuit diagram of an example of a portion of a respiration sensor.

Different types of circuitry can be incorporated into the NO generator 200 and its components. FIG. 4 shows a circuit diagram 400 of an example of a portion of a respiration sensor 208 that can be used to detect an inspiration. The respiration sensor 208 can monitor the temperature of the air in the airway. The respiration sensor can include a thermistor 402. The resistance of the thermistor 402 increases when it is cooled and decreases when it is warmed.

In this example, the respiration sensor 208 is set up as a voltage divider that includes the thermistor 402 and another resistor. An alternative configuration is to use a thermistor in a bridge configuration with other resistors. During inspiration, room or inspired temperature gas is inhaled past the thermistor 402. During expiration, gas that is typically warmer than room temperature (e.g., gas that is at or near body temperature) passes the thermistor 402. That is, during typical operation, the thermistor 402 increases in resistance during inspiration and decreases in resistance during expiration. The change in resistance of the thermistor 402 results in a varying voltage in the middle node of the voltage divider. This varying voltage may be modified by one or more amplifiers.

The respiration sensor 208 can include a differentiator that outputs a voltage that is proportional to the varying voltage of the voltage divider. This voltage can be sent to the controller 210 and converted into a digital voltage value. The controller 210 can use the digital voltage value to determine the start of an inspiration. Alternatively, the output of the differentiator can be modified by an amplifier and then fed into a Schmitt trigger. The Schmitt trigger can convert the voltage into a digital voltage value and create a hysteresis. The hysteresis can help differentiate between small temperature decreases seen late in an expiration period (which are to be ignored), and larger temperature decreases seen at the start of an inspiration period (which are of interest). The digital voltage value can be sent to the controller 210, which can recognize the start of an inspiration.

Figure 5:
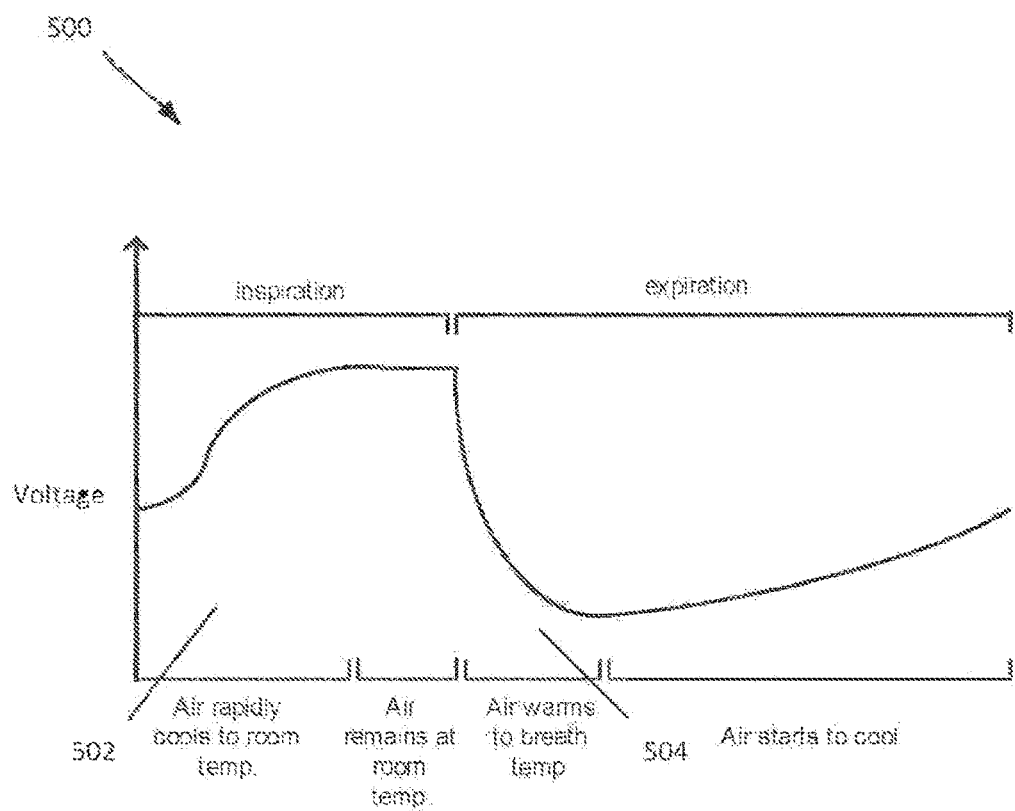
FIG. 5 depicts an example of a voltage time series from a respiration sensor.

FIG. 5 shows an example of a voltage time series 500 of a respiration sensor 208. As explained above, during inspiration, relatively cool inhaled gas passes the thermistor 402. The cool inspired gas causes the resistance of the thermistor to increases, which in turn causes the voltage at the middle node of the voltage divider to increase, as reflected in region 502. During expiration, relatively warm gas near core body temperature (approximately 37 degrees Celsius) passes by the thermistor 402. The warm gas causes the resistance of the thermistor to decrease, which in turn causes the voltage at the middle node of the voltage divider to decrease, as reflected in region 504.

In some examples, the respiration sensor 208 can be a tube contiguous with the area near the electrodes 206 that can sense pressure. Spontaneous inspiration is triggered by a lower airway and intrathoracic pressure, whilst mechanical ventilation produces a positive airway pressure (to inflate the lungs). Thus, pressure sensing of inspiration, whether positive (mechanical ventilation) or negative (spontaneous inspiration) could trigger the spark. In some examples, a hot wire anemometer or a pneumotachograph can sense respiratory timings and volume.

In some examples, a circumferential chest belt containing a resistor (e.g., mercury strain gauge) or impedance sensor could sense the expansion of the chest (or abdomen) and thereby trigger the spark to produce NO upon the onset of inspiration. In certain cases, if the patient is on a respirator, the mechanical respirator or ventilator can trigger the endotracheal or tracheostomy pulse of synthesizing electricity (because the ventilator can know the timing, tidal volume of the inspiration, and the inspired oxygen concentration) to produce the necessary amount of NO by sparks timed to the onset of ventilator inspiration.

In cases where the respiration sensor 208 does not measure temperature, the respiration sensor 208 can be configured to detect when an inspiration or expiration occurs. The respiration sensor 208 can also differentiate between an inspiration and an expiration. For example, the respiration sensor 208 can detect the air flow direction of air passing by the respiration sensor 208 to determine whether the air is being inspired or expired.

Results achieved with the NO generator 200 (and the NO generator mask 220 of FIG. 2B) are described herein.

Figure 6A:
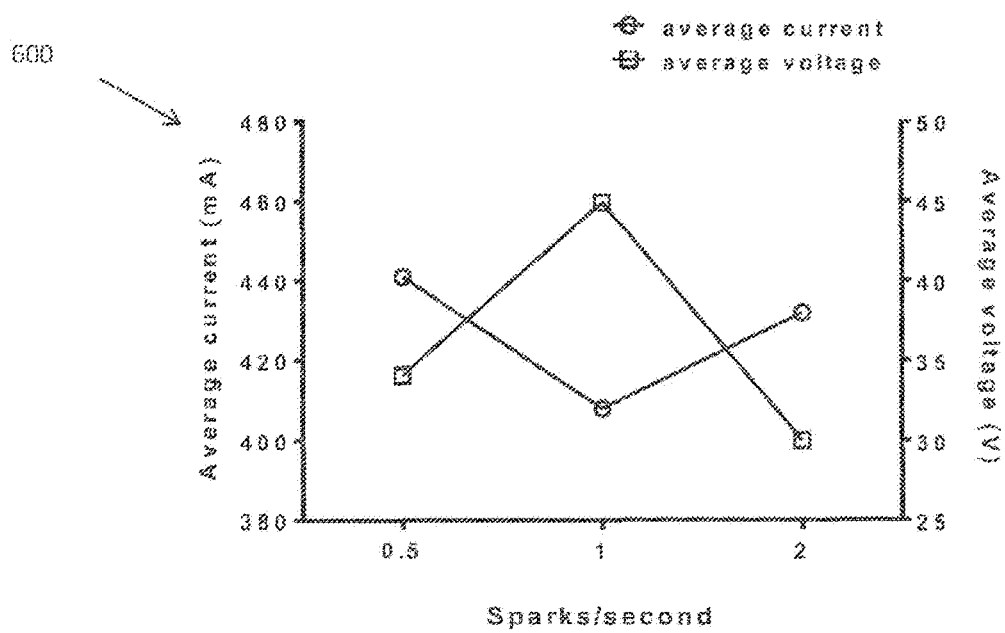
FIG. 6A shows average current and voltage as a function of sparks per second.
Figure 6B:
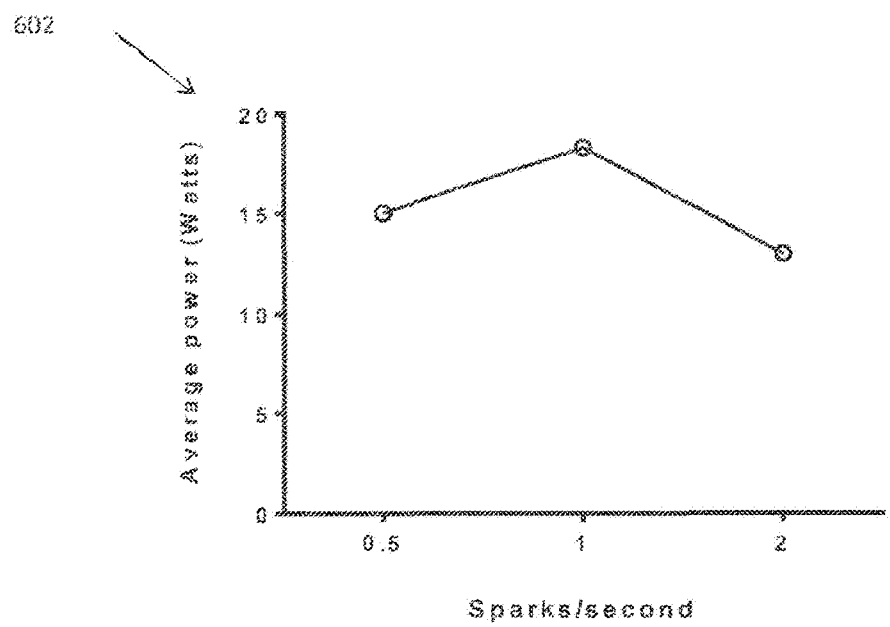
FIG. 6B shows average power as a function of sparks per second.
Figure 7A:
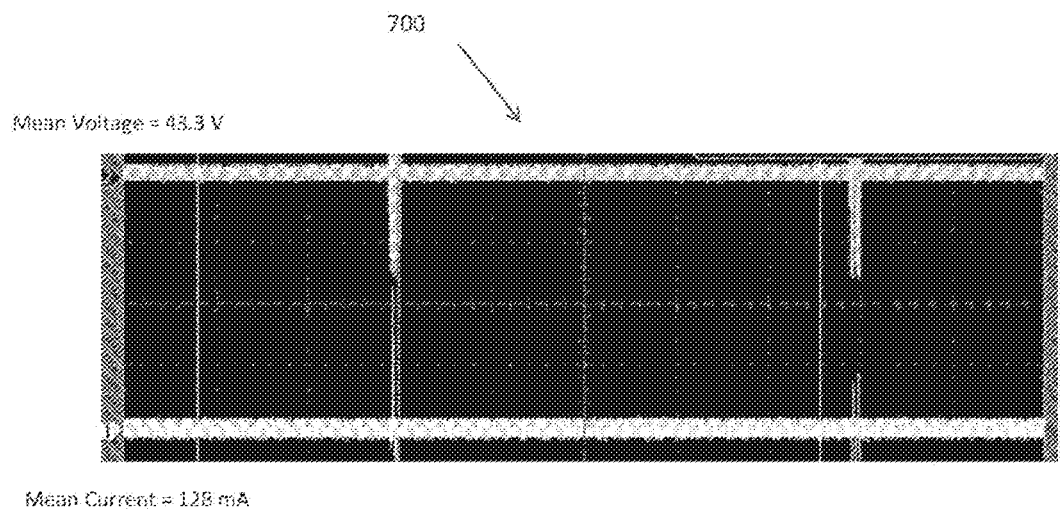
FIGS. 7A-B show tracings of voltage and current during two sparks of a 1 spark/second discharge.
Figure 7B:
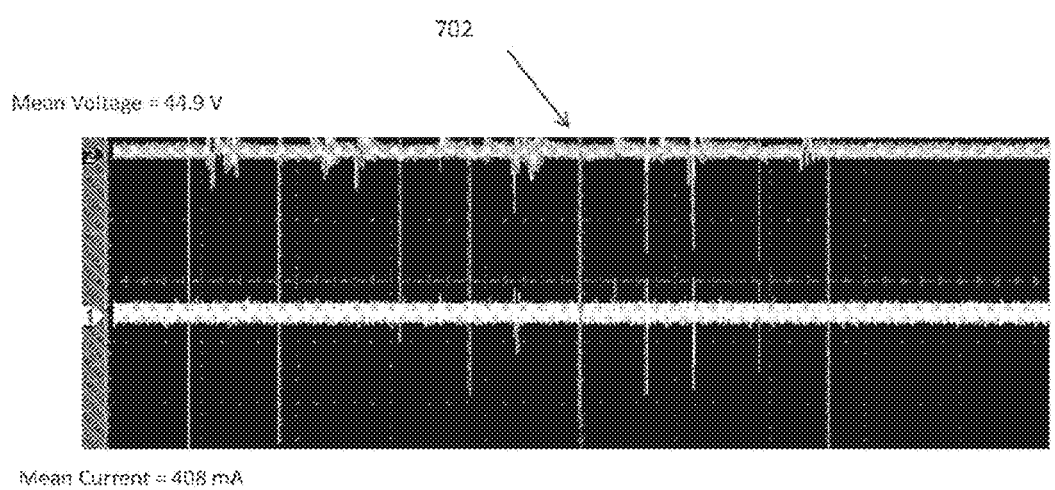

FIG. 6A is an average current and voltage chart 600 that shows the average current and voltage vs. sparks/second for NO generator 200. FIG. 6B is an average power chart 602 that shows the average power vs. sparks/second for NO generator 200. Average current and power peak between 0.5 and 2 sparks/second, and average voltage dips over the same range. FIG. 7A shows oscilloscope traces 700 for voltage (upper trace) and current (lower trace) during 2 sparks of a 1 spark/second discharge. FIG. 7B shows oscilloscope traces 702 for voltage (upper trace) and current (lower trace) traces for a 1 spark/second discharge with a spark duration (single spark) of 27 msec.

Animal Study 1

Four lambs weighing approximately 32 kg were studied. General anesthesia was induced with 5% inhaled isoflurane (1-chloro-2,2,2-trifluoroethyldifluromethyl ether, Baxter, Deerfield, Ill.) in oxygen via a mask and then maintained with 1-4% isoflurane at an initial inspired oxygen fraction ($FiO_2$) of 0.40. After tracheal intubation, animals were instrumented with indwelling carotid artery and pulmonary artery Swan-Ganz catheters.

All hemodynamic measurements were performed in the anesthetized lambs. All lambs were ventilated with a mechanical ventilator (model 7200, Puritan Bennett, Pleasanton, Calif.) at tidal volume 400 ml and rate 12 breaths/min.

To induce pulmonary hypertension, the potent pulmonary vasoconstrictor U46619 (Cayman Chemical, Ann Arbor, Mich.), the analog of the endoperoxide prostaglandin $H_2$, was infused intravenously at a rate of 0.8-0.9 µg/kg/min to increase the mean pulmonary artery pressure (PAP) to 30 mmHg.

To study the pulmonary vasodilator effect of nitric oxide (NO) produced by electric discharge, either a mini spark plug or iridium spark plug was placed in the inspiratory line of the sheep ventilator while airway gas flow measurements were measured by software (NICO Respironics, Wallingford, Conn.) to determine inspiration, expiration, and the tidal volume of each mechanical breath. Electrodes of the spark plug generated a series of sparks as described with reference to FIG. 3. In some studies, sparks were produced continuously throughout the respiratory cycle (continuous sparking). In other studies, sparks were produced on each breath commencing with inspiration, or shortly before inspiration began (intermittent sparking for 0.8 seconds/breath, 12-15 breaths/min). This was done to avoid wasted NO production during the expiratory phase of respiration.

FIG. 8 shows NO and $NO_2$ concentrations from an NO generator (e.g., NO generator 102 of FIG. 1) using various electrode materials. The test conditions included the use of a ¼" rod, an electrode gap of 2.0 mm, constant air flow at 5 L/min, and an $FiO_2$ of 0.21. For the tungsten electrode, B=40 pulse groups per second, N=30 sparks per pulse group, P=100 microseconds, and H=20 microseconds. For the nickel electrodes, B=35 pulse groups per second, N=40 sparks per pulse group, H=180 microseconds, and P=70 microseconds. For the iridium electrodes, B=35 pulse groups per second, N=40 sparks per pulse group, H=180 microseconds, and P=80 microseconds.

Figure 9:
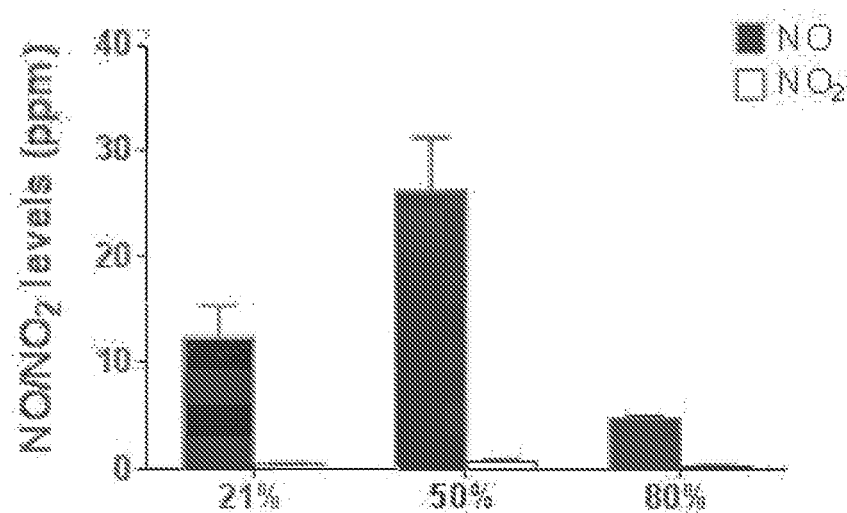
FIG. 9 shows NO and $NO_2$ concentrations at various reactant gas oxygen concentrations.

FIG. 9 shows NO and $NO_2$ concentrations at various reactant gas oxygen concentrations from the NO generator using mini spark plug (Micro Viper Z3 with 6 mm HEX and 10-40 THRD, Rimfire, Benton City, Wash.) with continuous sparking.

Figure 10:
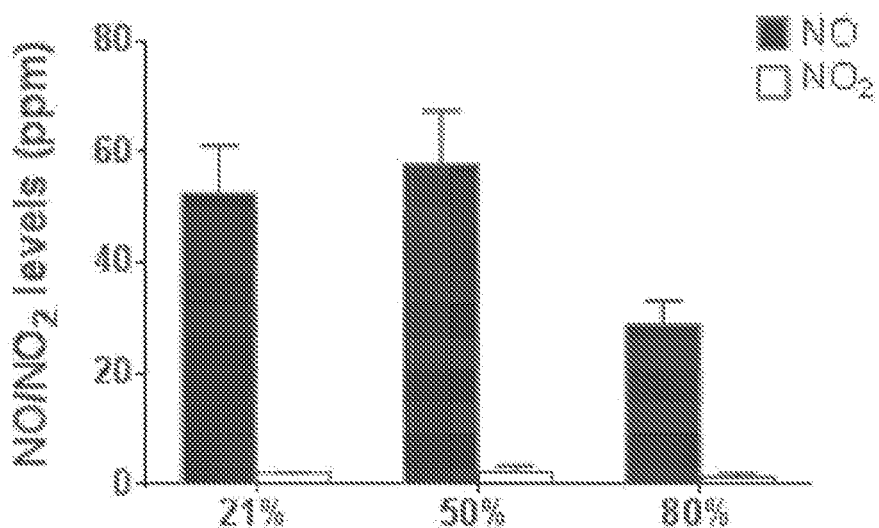
FIG. 10 shows NO and $NO_2$ concentrations at various reactant gas oxygen concentrations.

FIG. 10 shows NO and $NO_2$ concentrations at various reactant gas oxygen concentrations from the NO generator using an iridium spark plug (ACDelco 41-101, Waltham, Mass.) with continuous sparking.

Figure 11:
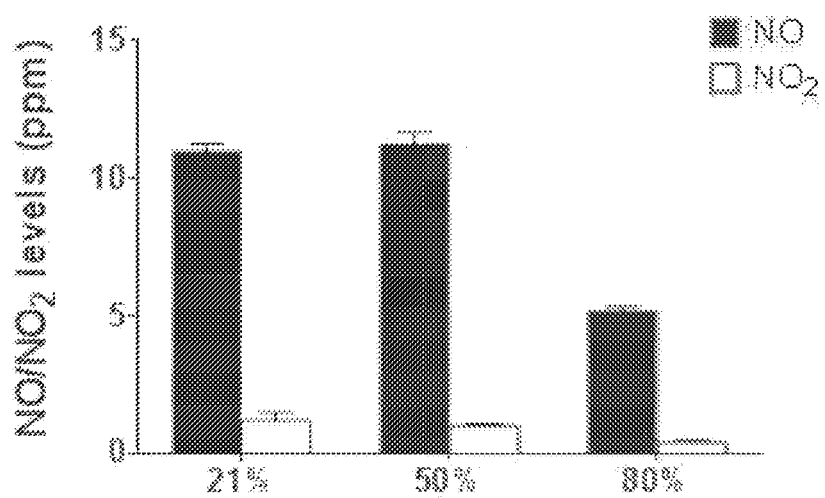
FIG. 11 shows NO and $NO_2$ concentrations at various reactant gas oxygen concentrations.

FIG. 11 shows NO and $NO_2$ concentrations at various reactant gas oxygen concentrations from the NO generator using iridium spark plug with intermittent sparking.

Ozone ($O_3$) is a powerful oxidant that has many industrial and consumer applications related to oxidation. However, its oxidizing potential is high, and it is a toxic gas causing damage to mucus membranes and respiratory tissues in animals, and also to tissues in plants. This makes ozone a potent respiratory hazard and pollutant near ground level. Ozone is formed from atmospheric electrical discharges, and reacts with NO to form nitric dioxide ($NO_2$) and $O_2$ or reacts with $N_2$ to produce NO and $O_2$. In some examples, ozone levels are greater with continuous sparking than with intermittent sparking, and also increase with increasing $O_2$ concentrations.

Figure 12:
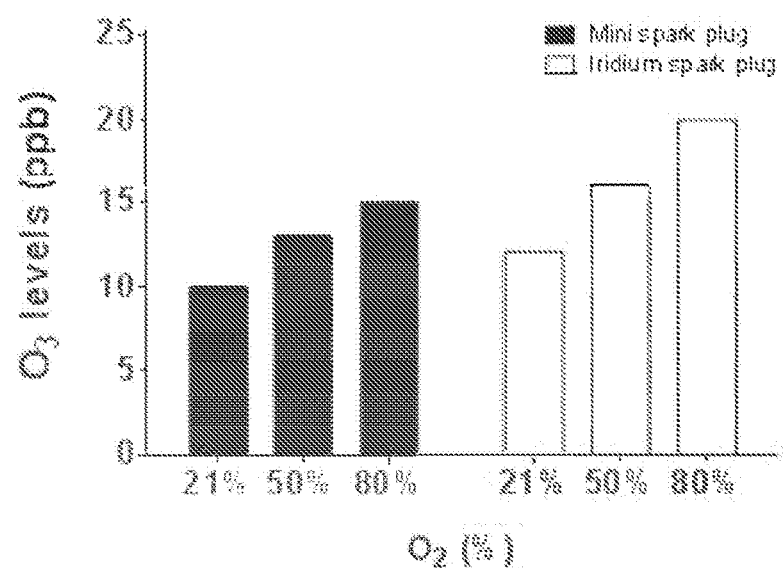
FIG. 12 shows ozone levels at various oxygen concentrations.

FIG. 12 shows $O_3$ levels at various $O_2$ concentrations using the mini spark plug and iridium spark plug with continuous sparking. In this example, B=60 pulse groups per second, N=50 sparks per pulse group, P=140 microseconds, H=40 microseconds, and air flow rate is 5 L/min.

Figure 13:
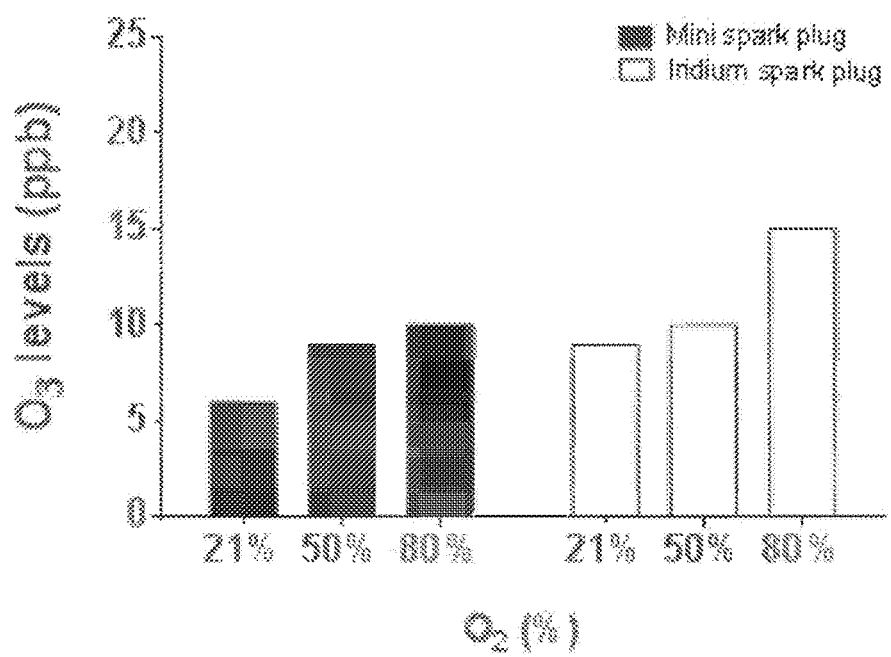
FIG. 13 shows ozone levels at various oxygen concentrations.

FIG. 13 shows $O_3$ levels at various $O_2$ concentrations using the mini spark plug and iridium spark plug with intermittent sparking triggered on each breath commencing with inspiration, or shortly before inspiration began. In this example, B=60 pulse groups per second, N=50 sparks per pulse group, P=140 microseconds, H=40 microseconds, and air flow rate is 5 L/min.

Figure 14:
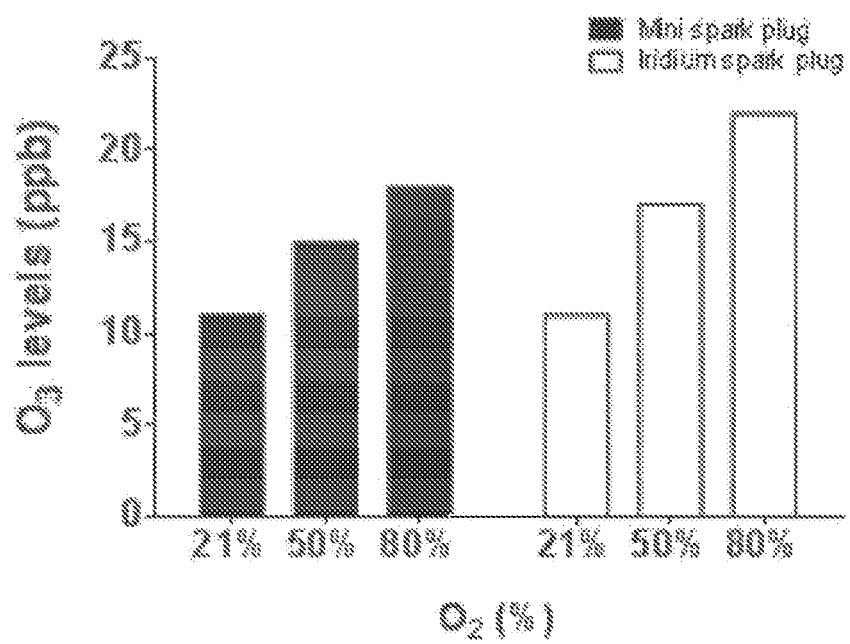
FIG. 14 shows ozone levels at various oxygen concentrations.

FIG. 14 shows $O_3$ levels at various $O_2$ concentrations using the mini spark plug and iridium spark plug with continuous sparking. In this example, B=35 pulse groups per second, N=25 sparks per pulse group, P=240 microseconds, H=100 microseconds, and air flow rate is 5 L/min.

Figure 15:
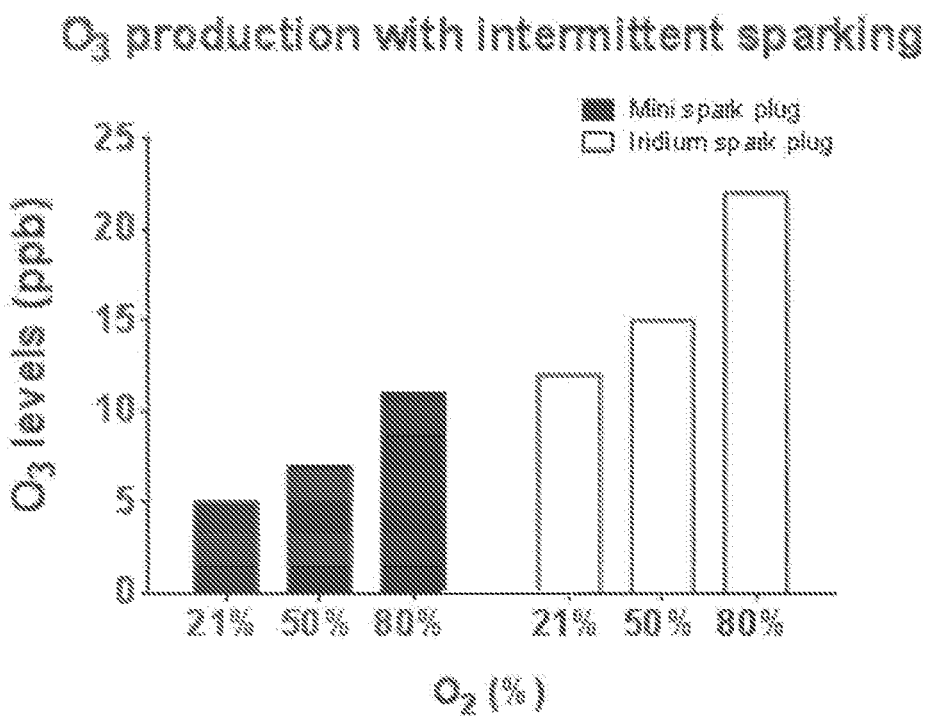
FIG. 15 shows ozone levels at various oxygen concentrations.

FIG. 15 shows $O_3$ levels at various $O_2$ concentrations using the mini spark plug and iridium spark plug with intermittent sparking triggered on each breath commencing with inspiration, or shortly before inspiration began. In this example, B=35 pulse groups per second, N=25 sparks per pulse group, P=240 microseconds, H=100 microseconds, and air flow rate is 5 L/min.

Figure 16:
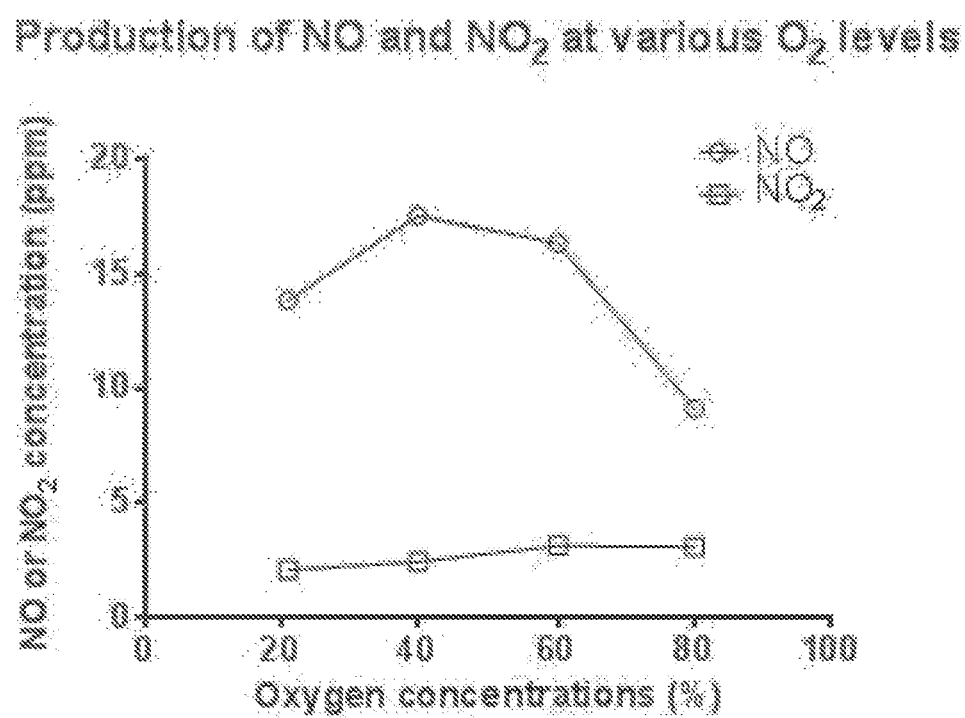
FIG. 16 shows NO and $NO_2$ concentrations at various reactant gas oxygen concentrations.

FIG. 16 shows NO and NO2 concentrations at various reactant gas oxygen concentrations using an oxygen concentrator. In this example, B=5 pulse groups per second, N=25 sparks per pulse group, P=200 microseconds, H=60 microseconds, and air flow rate is 5 L/min.

Figure 17:
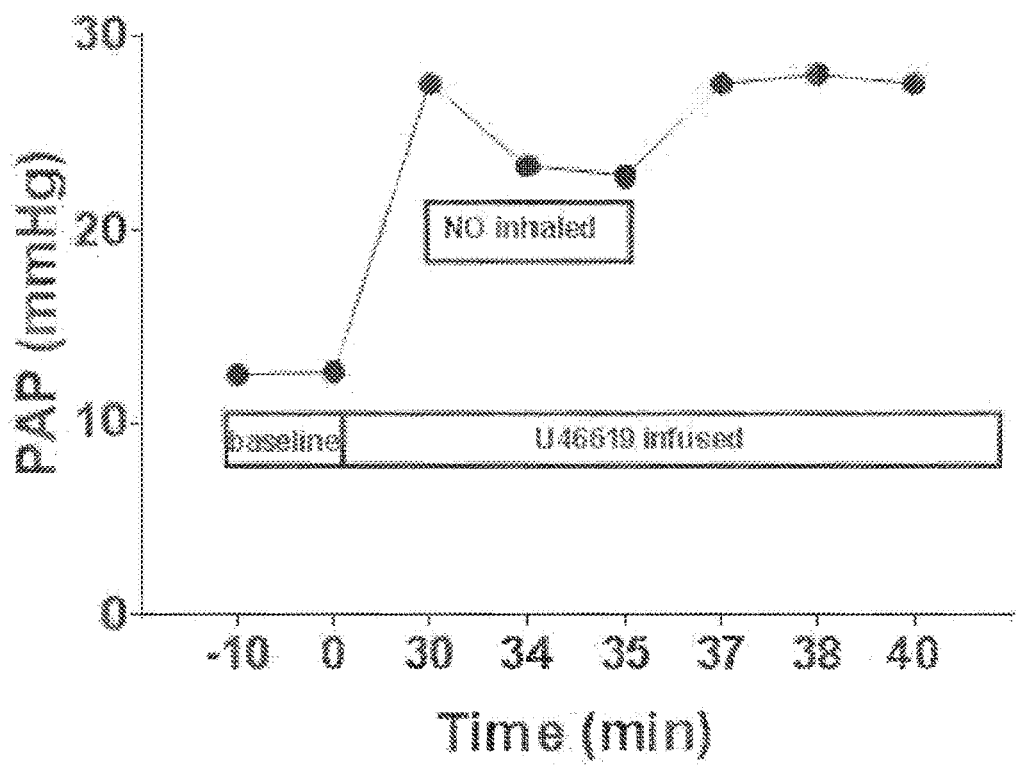
FIG. 17 shows mean pulmonary artery pressure over an infusion period.

FIG. 17 shows mean pulmonary artery pressure (PAP) during infusion of U46619. At baseline, before U46619 infusion was begun, the PAP was 14 mmHg. Over 30 minutes of infusion, the mean PAP increased to 28 mmHg. After PAP was stable, sparks were generated at the beginning of each inspiration for a period of four minutes. Over the four minute period, the PAP was significantly decreased to 22 mmHg. After ceasing sparking and waiting a four minute period, mean PAP again rose to 28 mmHg. In this example, B=60 pulse groups per second, N=100 sparks per pulse group, P=140 microseconds, H=17 microseconds, and tidal volume (Vt)=400 ml.

Figure 18:
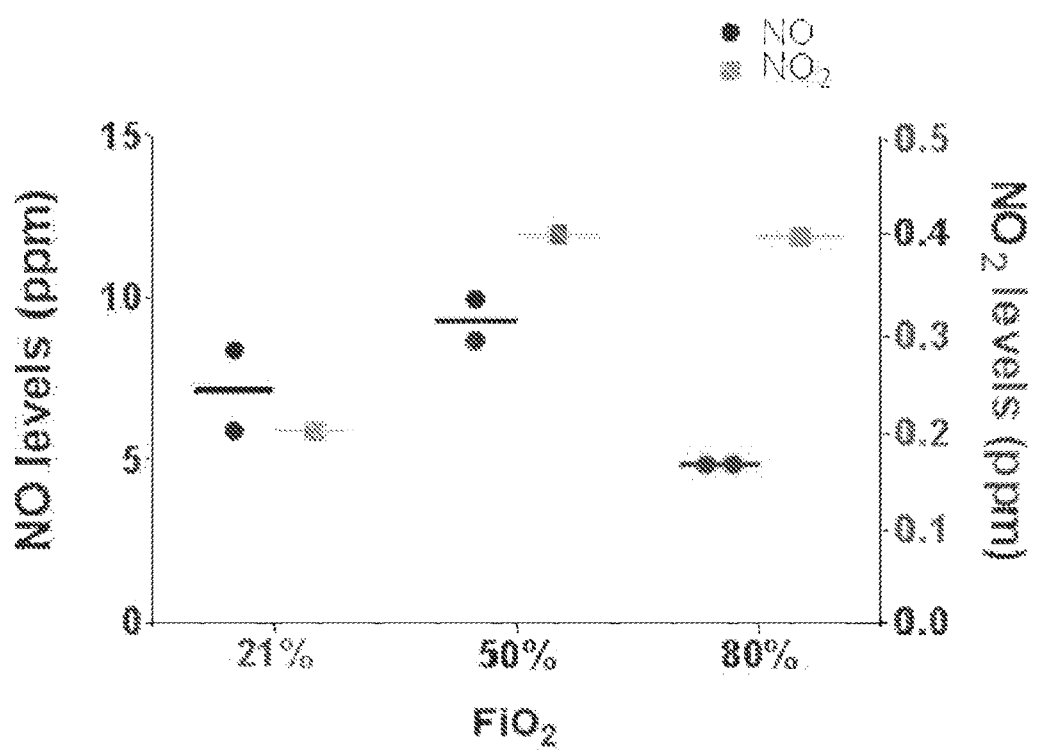
FIG. 18 shows NO and $NO_2$ concentrations at various $FiO_2$.

FIG. 18 shows NO and $NO_2$ concentrations at various $FiO_2$ while producing intermittent sparks triggered by inspiratory flow using an iridium spark plug.

Figure 19:
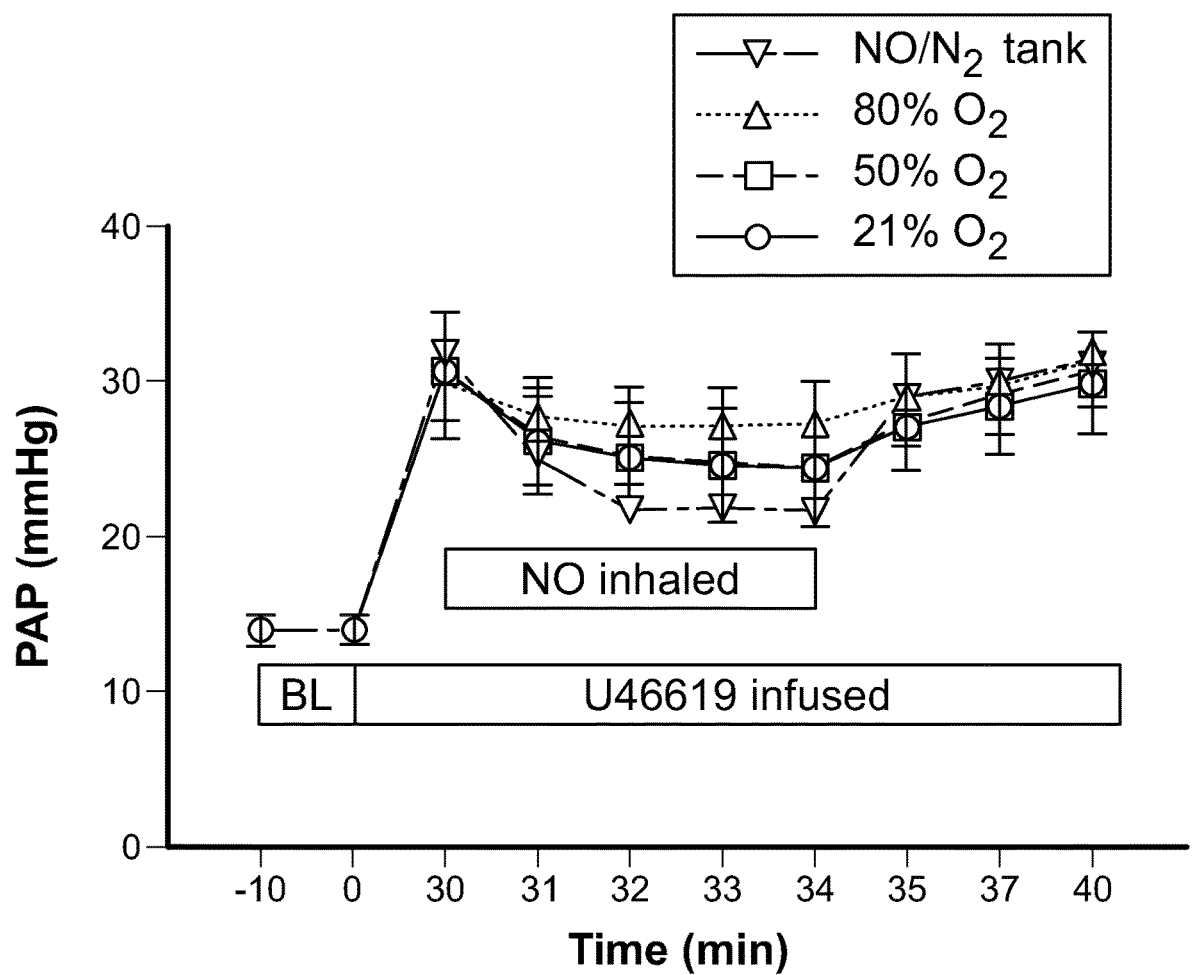
FIG. 19 shows mean pulmonary artery pressure at various $FiO_2$.

FIG. 19 shows mean PAP at various $FiO_2$ levels during U46619 infusion before and after producing intermittent sparks. In these examples, B=35 pulse groups per second, N=25 sparks per pulse group, P=240 microseconds, H=100 microseconds, and Vt=400 ml.

Figure 20:
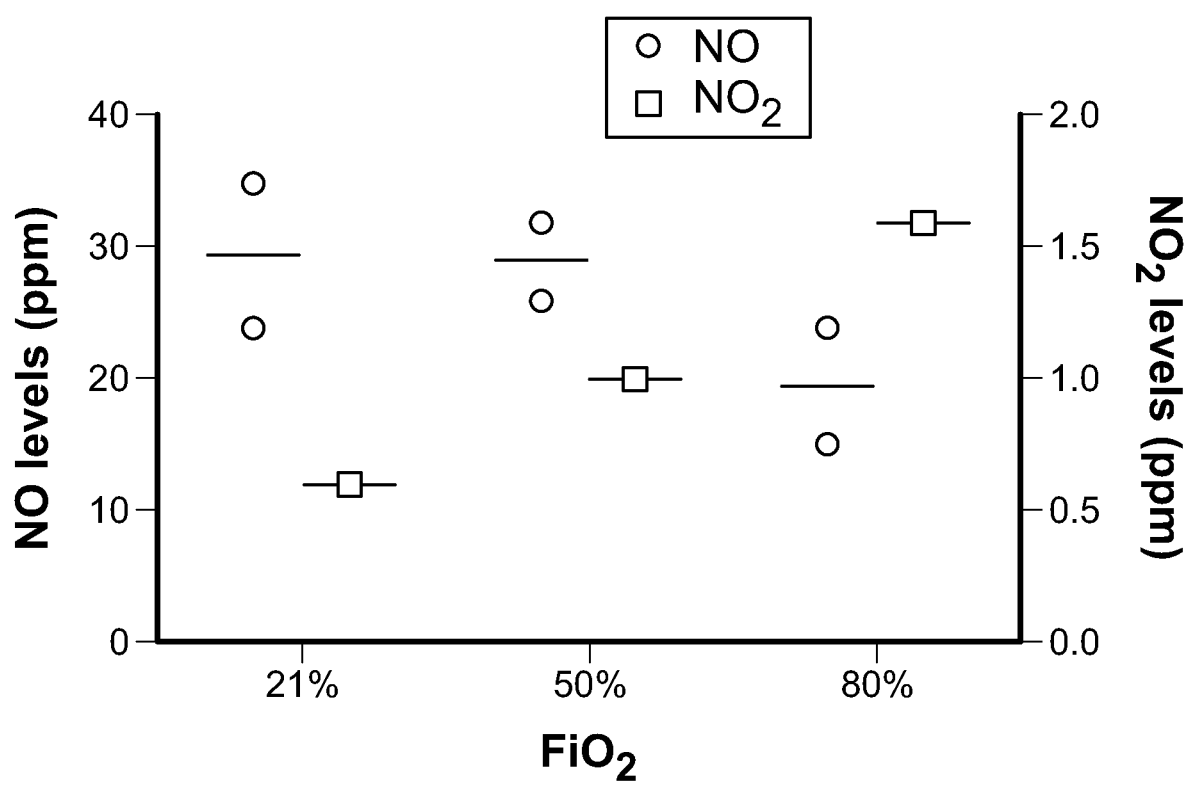
FIG. 20 shows NO and $NO_2$ concentrations at various $FiO_2$.
Figure 21:
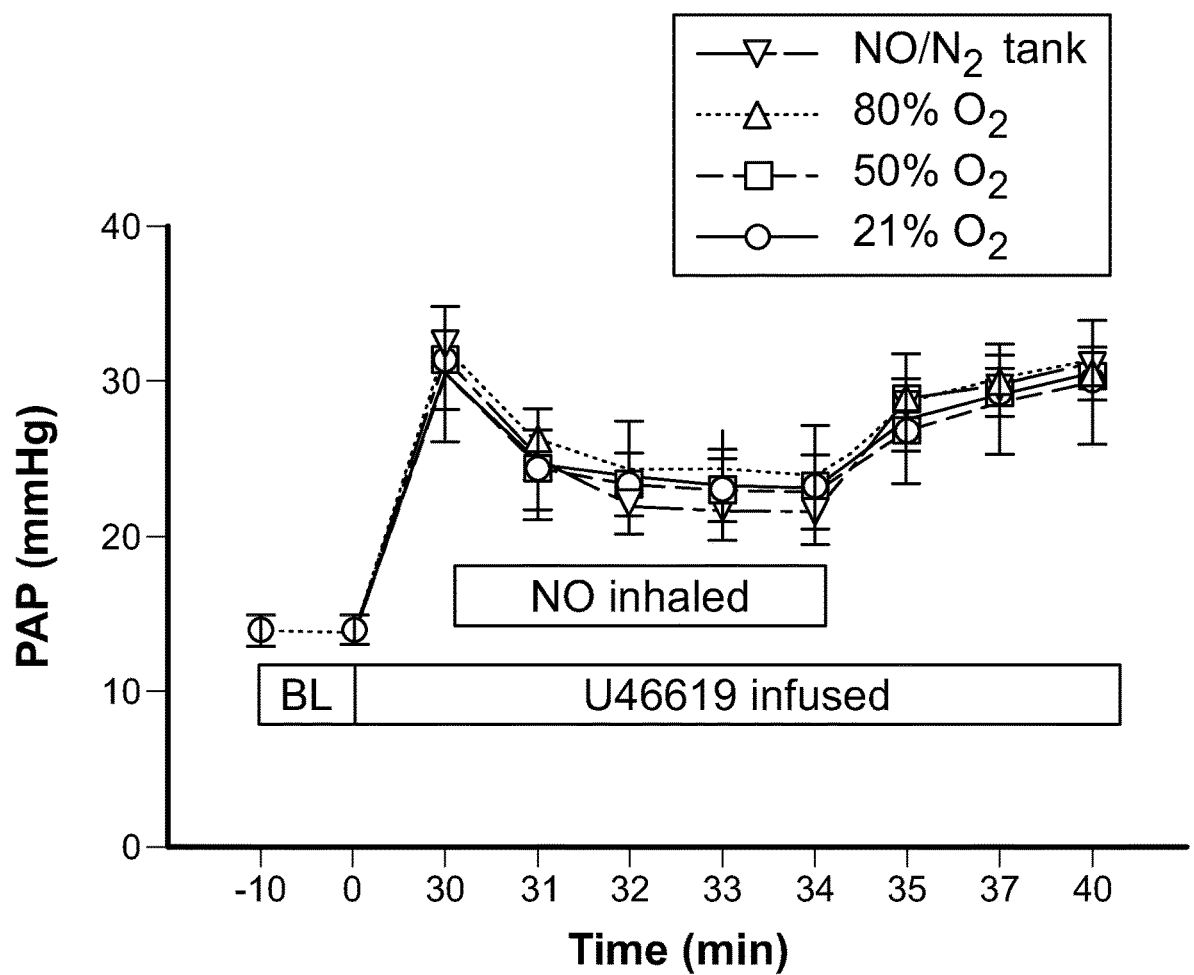
FIG. 21 shows mean pulmonary artery pressure at various $FiO_2$.

FIG. 20 shows NO and $NO_2$ concentrations at various $FiO_2$ levels while producing continuous sparks triggered upon inspiratory flow using an iridium spark plug. FIG. 21 shows PAP at various $FiO_2$ levels during infusion of U46619 before and after producing continuous sparks. In these examples, B=35 pulse groups per second, N=25 sparks per pulse group, P=240 microseconds, H=100 microseconds, and Vt=400 ml.

Figure 22:
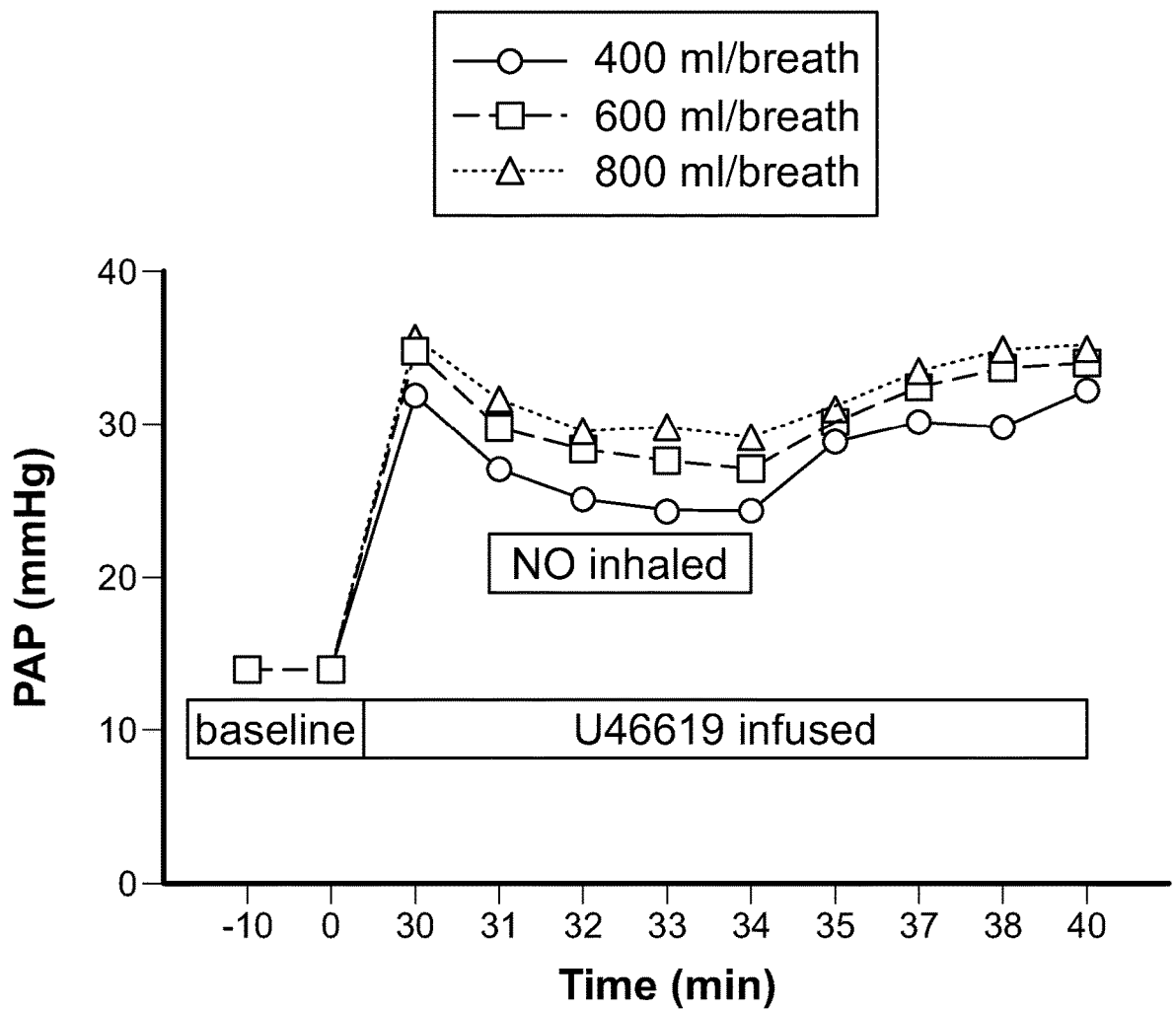
FIG. 22 shows mean pulmonary artery pressure at various tidal volumes.
Figure 23:
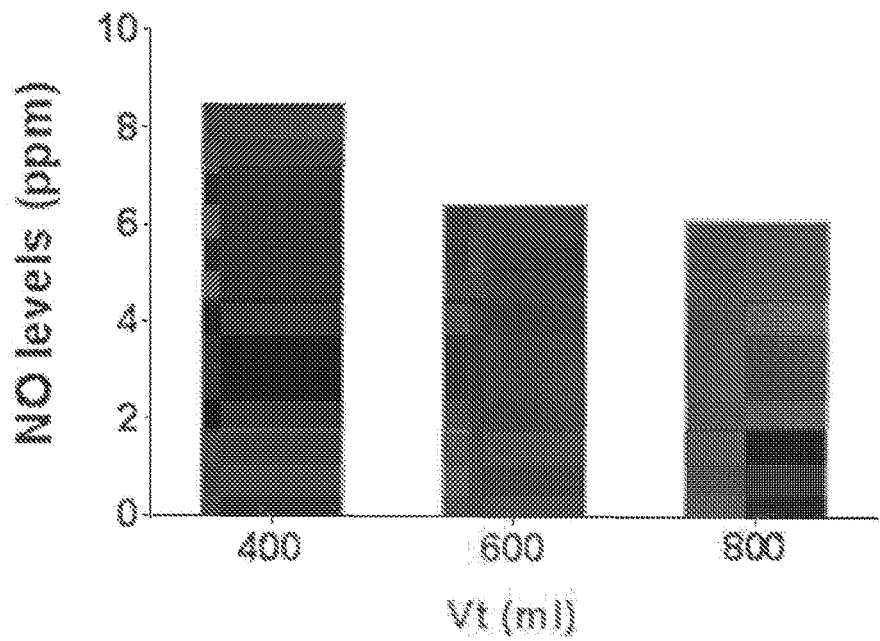
FIG. 23 shows NO and $NO_2$ concentrations at various tidal volumes.

In some further examples, smaller breath sizes produce higher levels of NO because of reduced dilution of spark synthesized NO. FIG. 22 shows mean PAP at various Vt (respiratory tidal volume levels) during infusion of U46619 before and after producing NO with sparks triggered by inspiratory flow using an iridium spark plug. FIG. 23 shows NO and $NO_2$ concentrations in lambs at the various levels of tidal volume ventilation (Vt). In these examples, B=35 pulse groups per second, N=25 sparks per pulse group, P=240 microseconds, H=100 microseconds, and $FiO_2$=0.21.

Figure 24:
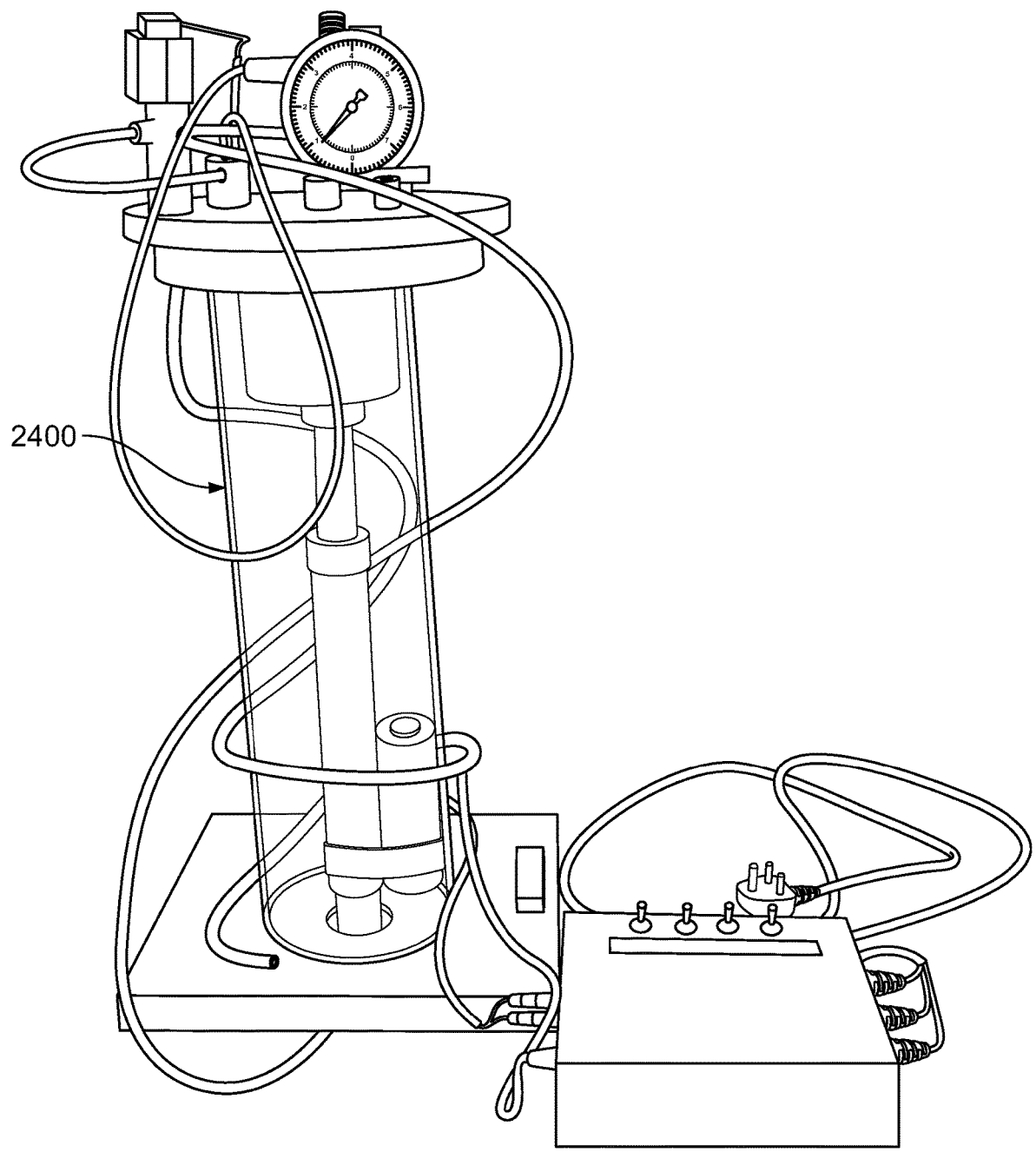
FIG. 24 shows a test setup for measuring NO and NO2 levels in a hypobaric chamber at various atmospheric pressures.
Figure 25:
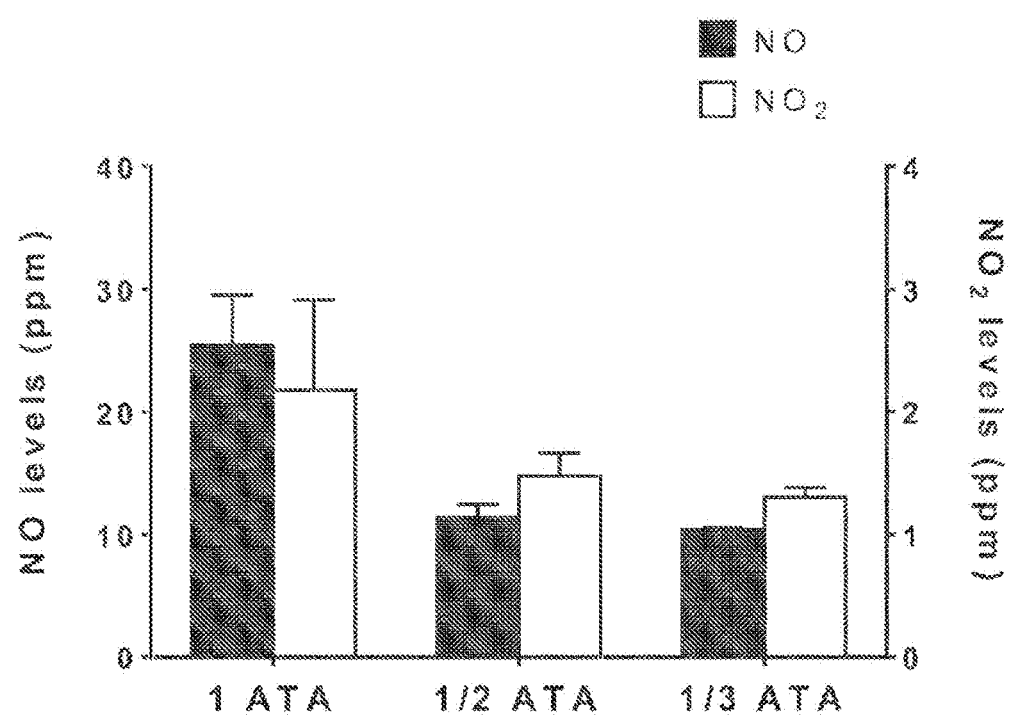
FIG. 25 shows NO and $NO_2$ levels at various atmospheric pressures.

FIG. 24 shows a test setup for measuring NO and $NO_2$ levels in a hypobaric chamber 2400 at various atmospheric pressures. The results of the test are shown in FIG. 25. To create a negative pressure (e.g., ½ ATA, ⅓ ATA) inside the hypobaric chamber 2400, inlet and outlet valves were closed and a piston was translated away from the spark plug. The spark plug was then fired for 30 seconds. In this example, B=100 pulse groups per second, N=10 sparks per pulse group, P=140 microseconds, and H=10 microseconds. The piston was then translated toward the spark plug to bring the pressure in the hypobaric chamber 2400 back to 1 ATA. The outlet valve was opened, and gas samples were collected in a 3 L respiratory bag by further translating the piston toward the spark plug. The collected gas samples were analyzed with Sievers NOA i280 immediately after collection.

Animal Study 2

A mini spark plug (Micro Viper Z3 with 6 mm HEX and 10-40 THRD, Rimfire, Benton City, Wash.) was installed in the airway of sheep #1. The mini spark plug was triggered by a respiration sensor that measured the change in inspired gas temperature upon inspiration. Electrodes of the mini spark plug generated a series of sparks as described with reference to FIG. 3.

Figure 26:
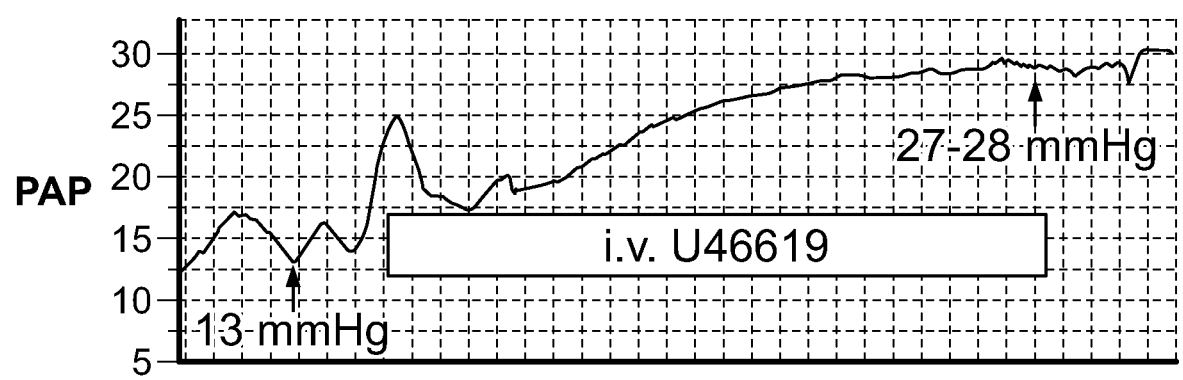
FIG. 26 shows mean pulmonary artery pressure over an infusion period.

FIG. 26 shows PAP during an infusion of U46619 for a period of time. U46619 was IV infused at a concentration of 50 μg/ml at a rate of 18 ml/hour. At baseline, the mean PAP was 13 mmHg. Over 30 minutes of infusion, the mean PAP increased to 27-28 mmHg.

Figure 27:
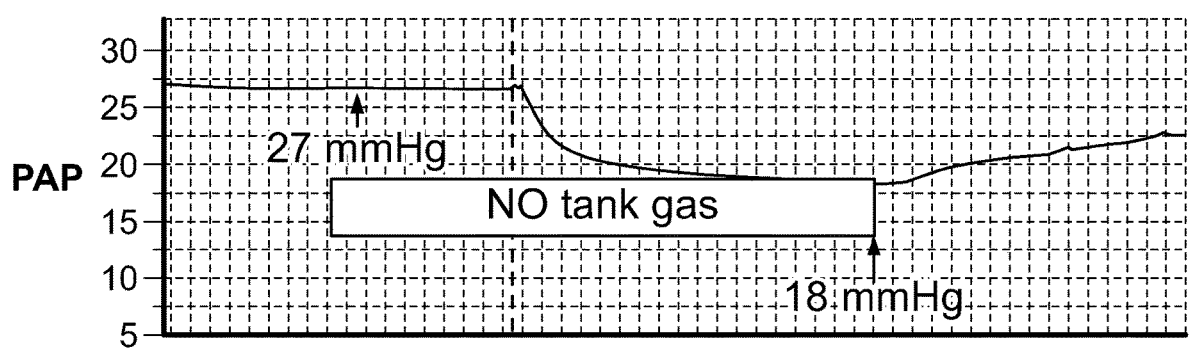
FIG. 27 shows mean pulmonary artery pressure while breathing NO.

FIG. 27 shows mean PAP while the sheep is breathing NO at a concentration of 40 ppm from a tank. The mean PAP decreased to 18 mmHG after two minutes.

Figure 28:
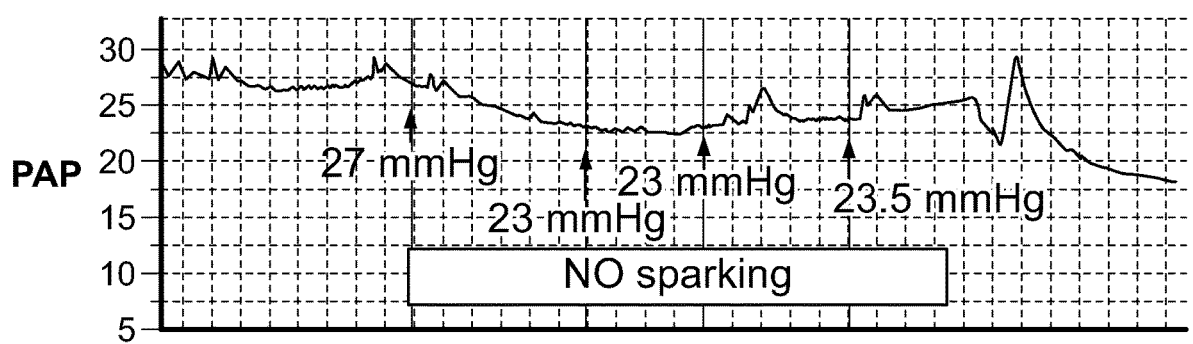
FIG. 28 shows mean pulmonary artery pressure during sparking triggered upon inspiration.

FIG. 28 shows mean PAP during sparking triggered by inspiratory breathing (e.g., triggered by the NICO a respiration sensor upon inspiration). In this example, B=1 pulse groups per second, N=70 sparks per pulse group, P=140 microseconds, and H=40 microseconds. In vitro at 200 ml/min, the NO concentration measured by chemiluminescence was 25 ppm.

Figure 29:
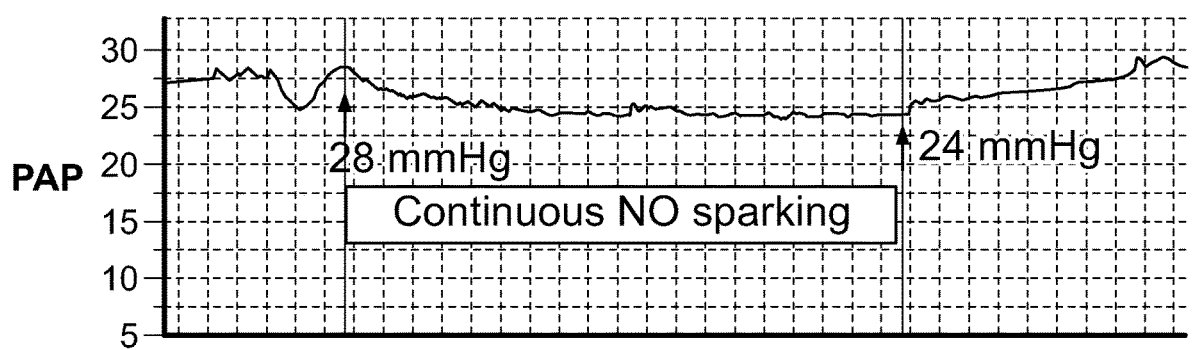
FIG. 29 shows mean pulmonary artery pressure during continuous sparking.

FIG. 29 shows mean PAP during continuous sparking. In this example, B=1 pulse groups per second, N=407 sparks per pulse group, P=140 microseconds, and H=40 microseconds. In vitro at 200 ml/min, the NO concentration was 125 ppm.

Figure 30:
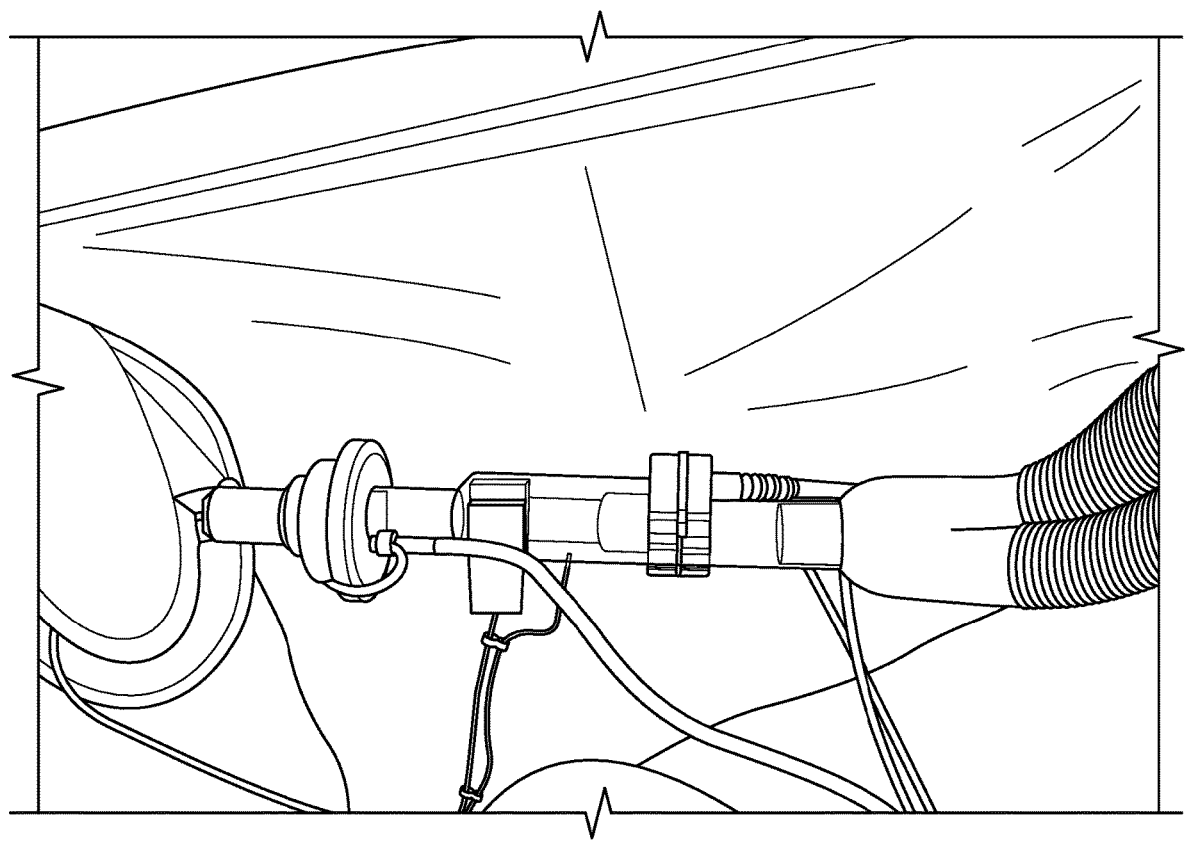
FIG. 30 shows a spark plug installed in a sheep's airway.

A mini spark plug was installed in sheep #2's airway, as shown in FIG. 30. The mini spark plug was triggered by a respiration sensor that measured the change in inspired gas temperature upon inspiration. Electrodes of the mini spark plug generated a series of sparks as described with reference to FIG. 3.

Figure 31:
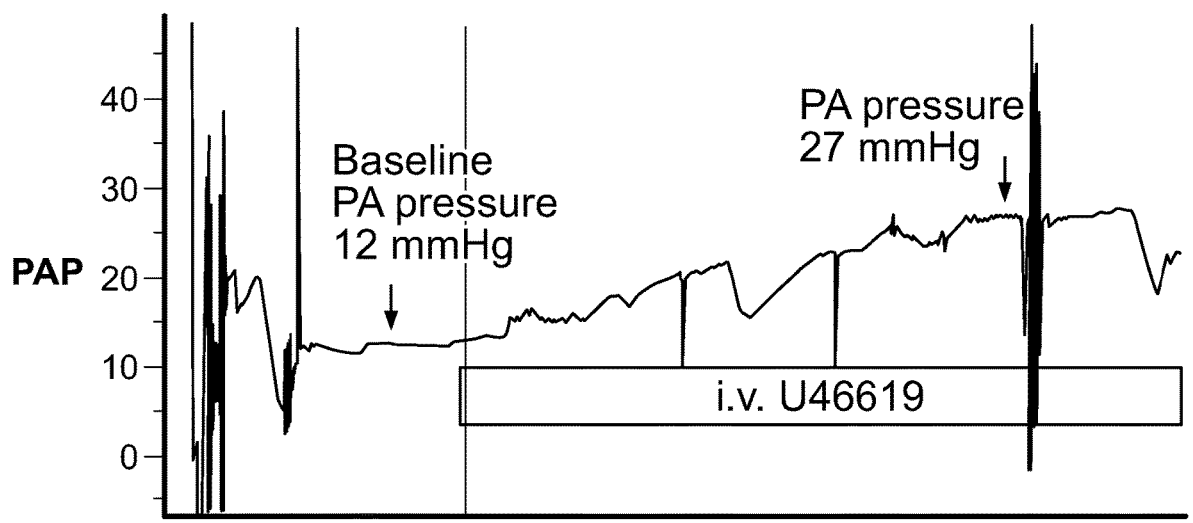
FIG. 31 shows mean pulmonary artery pressure during an infusion period of the pulmonary vasoconstrictor U46619.

FIG. 31 shows mean PAP during infusion of U46619 for a period of time. U46619 was infused at 50 μg/ml at 18 ml/hour. At baseline, the mean PAP was 12 mmHg. Over 30 minutes of infusion, the mean PAP increased to 27 mmHG.

Figure 32:
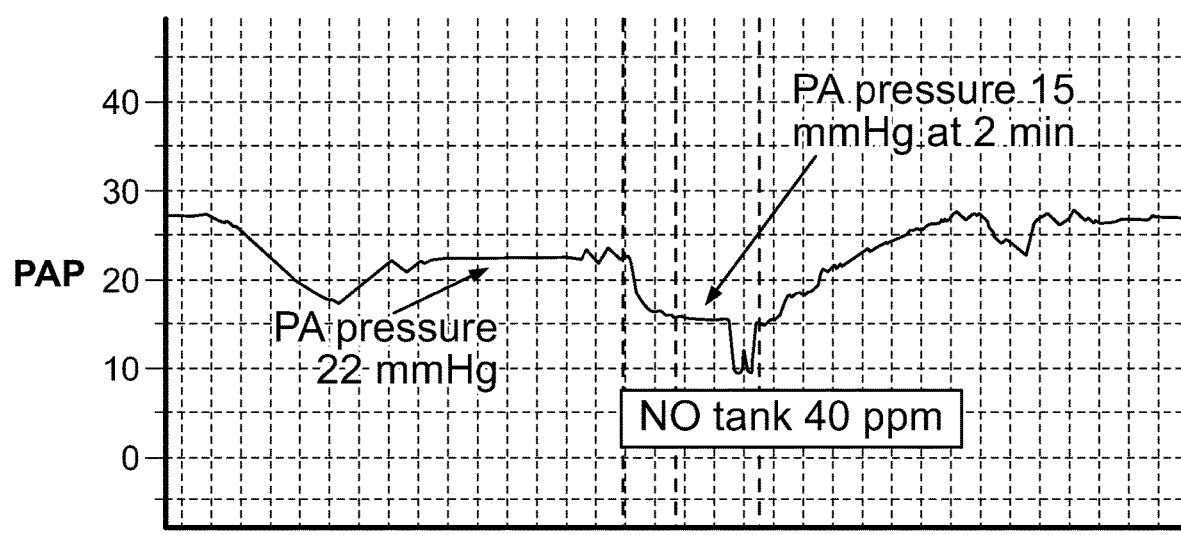
FIG. 32 shows mean pulmonary artery pressure while breathing NO.

FIG. 32 shows mean PAP while the sheep is breathing NO at a fixed concentration of 40 ppm delivered from a cylinder. The mean PAP decreased to 15 mmHg after two minutes.

Figure 33:
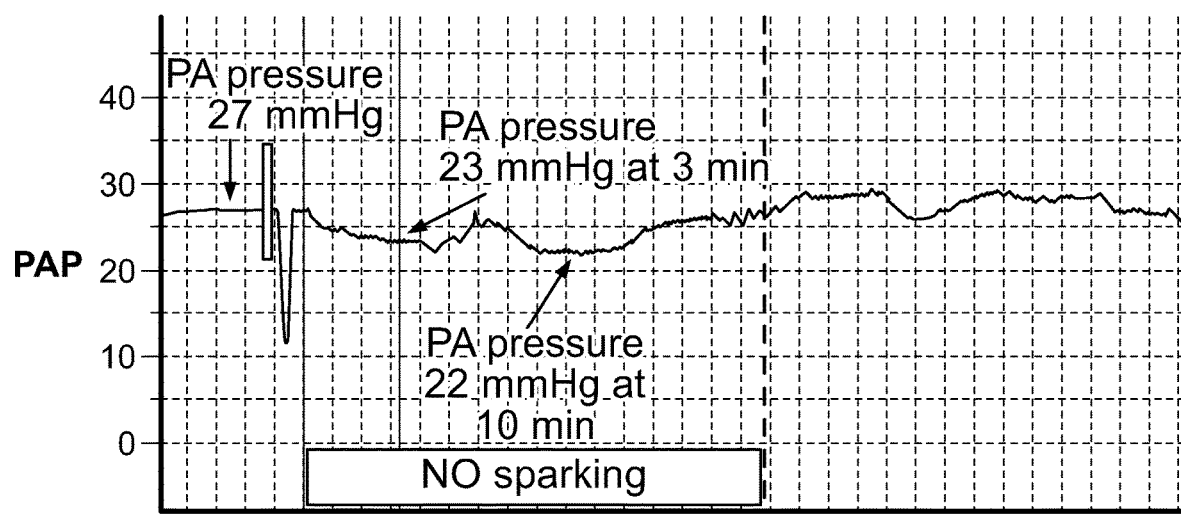
FIG. 33 shows mean pulmonary artery pressure during sparking triggered upon inspiration.

FIG. 33 shows mean PAP during sparking triggered by inspiratory breathing (e.g., triggered by a NICO respiration sensor upon inspiration) with flow control. In this example, B=60 pulse groups per second, N=100 sparks per pulse group, P=140 microseconds, and H=17 microseconds.

Bench Test

Figure 34:
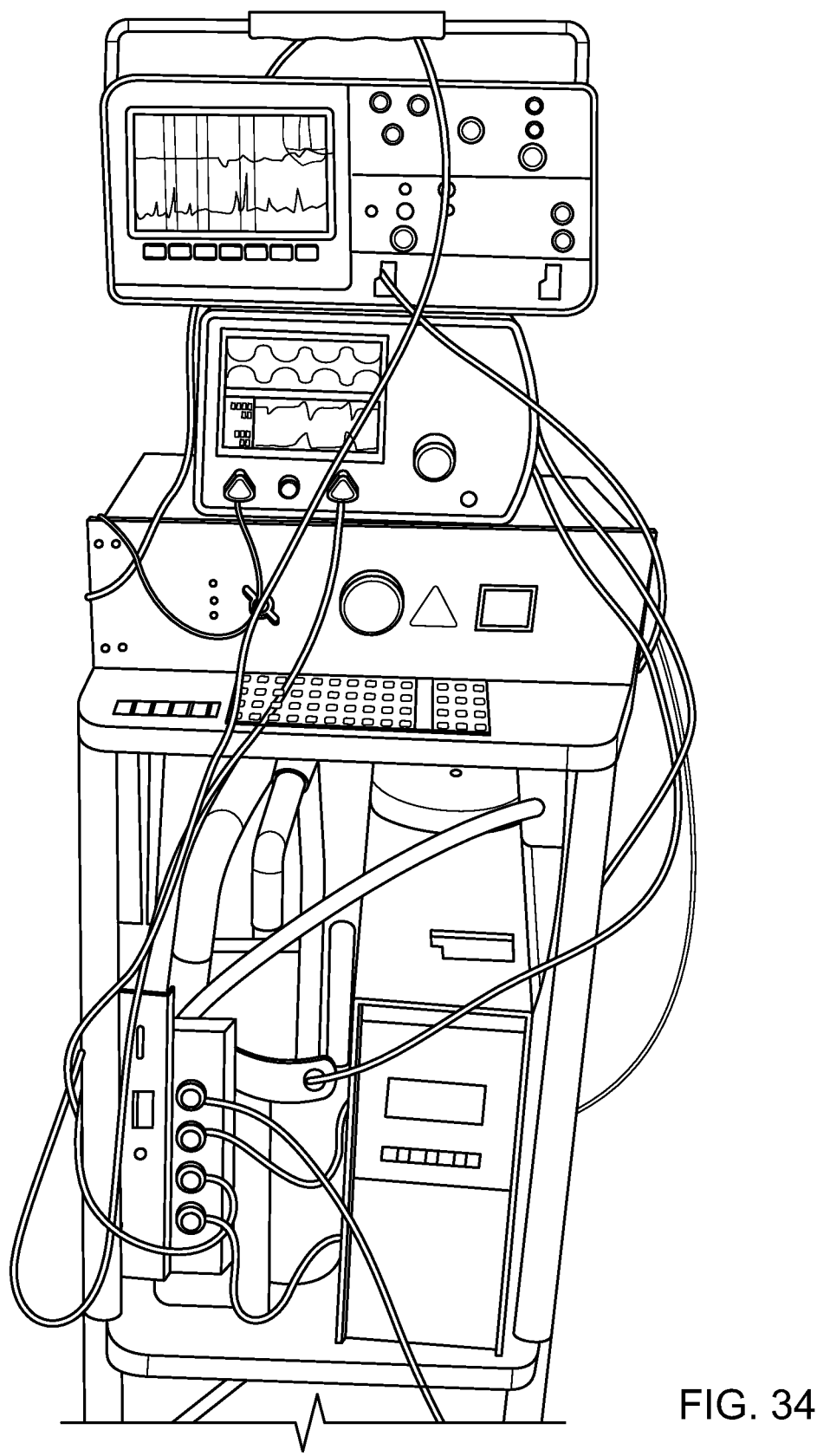
FIG. 34 shows a bench test setup with a sheep airway simulator.

FIG. 34 shows a bench test setup using a micro spark plug triggered by inspiration (flow controlled, NICO monitor) with a sheep airway simulator.

Figure 36:
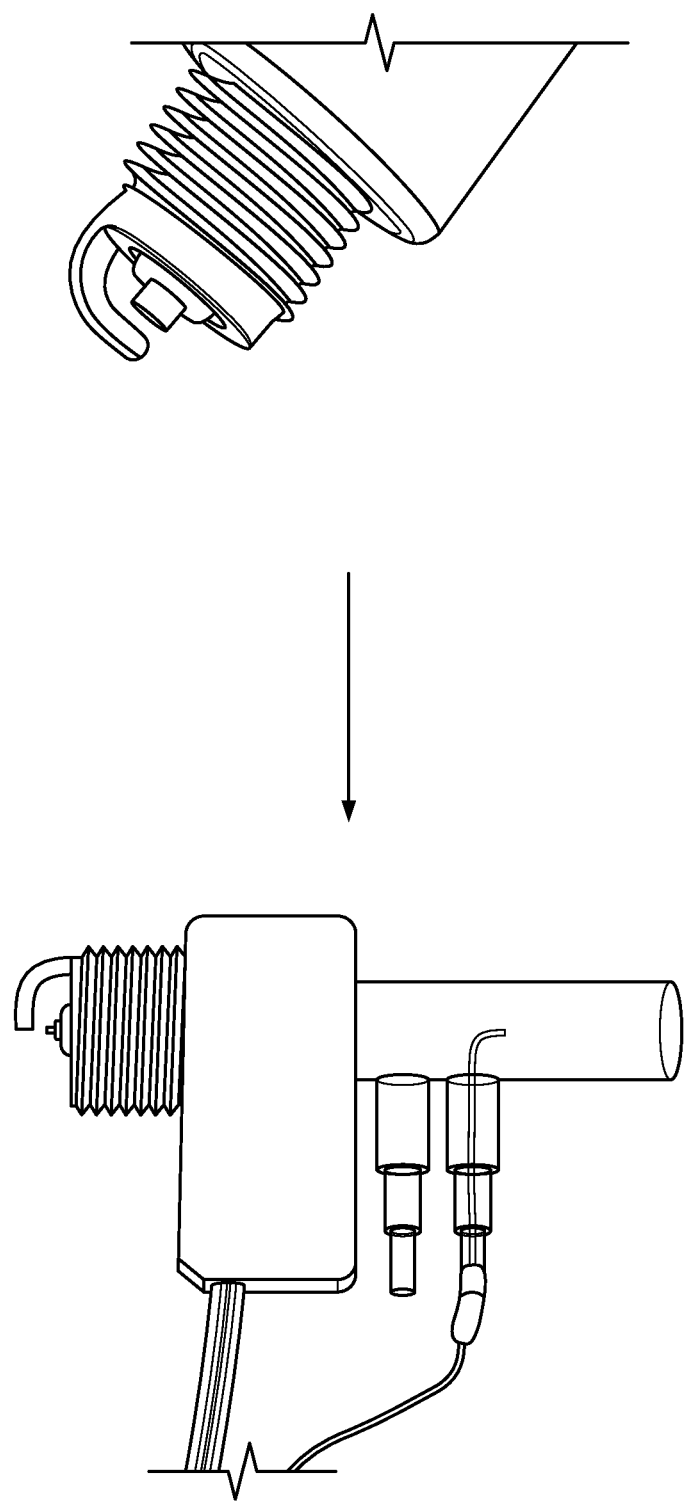
FIG. 36 shows a modified mini spark plug with a circuit gap.

FIG. 35 shows NO production under a constant reactant gas flow rate of 1 L/min using a modified mini spark plug with a circuit gap (as shown in FIG. 36) under various conditions. In this example, H was increased from 10 to 17. Continuous sparking in air produced major amounts of NO (i.e., approximately 250 ppm). The tang electrode of the mini spark plug was removed during modification to increase the electrode gap from 0.4 mm to 1.1 mm.

Figure 37:
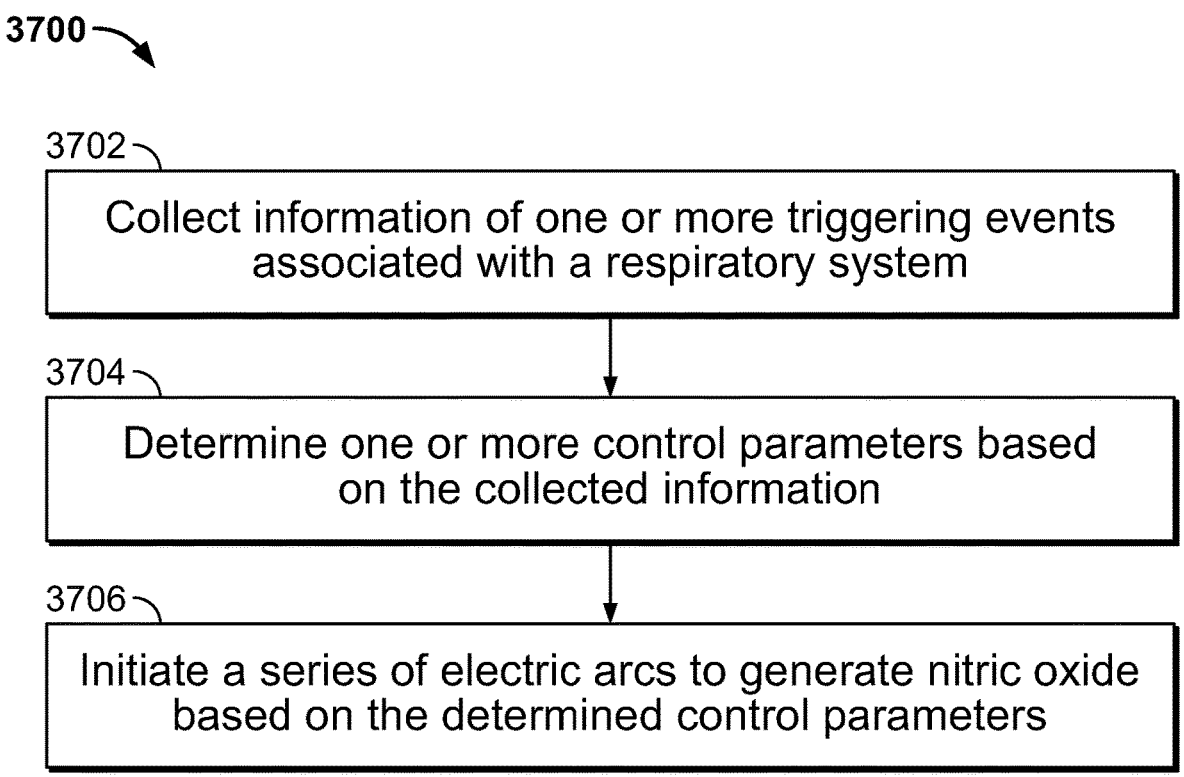
FIG. 37 is a flowchart.

Referring to FIG. 37, a flowchart 3700 represents an arrangement of operations of the controller (e.g., controller 210, shown in FIG. 2A). Typically, the operations are executed by a processor present in the controller. However, the operations may also be executed by multiple processors present in the controller. While typically executed by a single controller, in some arrangements, operation execution may be distributed among two or more controllers.

Operations include collecting 3702 information related to one or more triggering events associated with a respiratory system. For example, the respiration sensor 208 of FIG. 2A can collect information related one or more triggering events associated with a respiratory system. The information can include the onset time of an inspiration and the tidal volume of an inspiration (e.g., obtained from a NICO device, a hotwire anemometer, a pneumotachograph, etc.). The triggering event may be an inspiration. Operations also include determining 3704 one or more control parameter based on the collected information. For example, the controller 210 of FIG. 2A can determine one or more control parameters. The control parameters may create a pulse train. Operations also include initiating 3706 a series of electric arcs to generate nitric oxide based on the determined control parameters. For example, the electrodes 206 of FIG. 2A can initiate a series of electric arcs to generate nitric oxide based on the determined control parameters. The control parameters may control the timings of the series of electric arcs.

Figure 38:
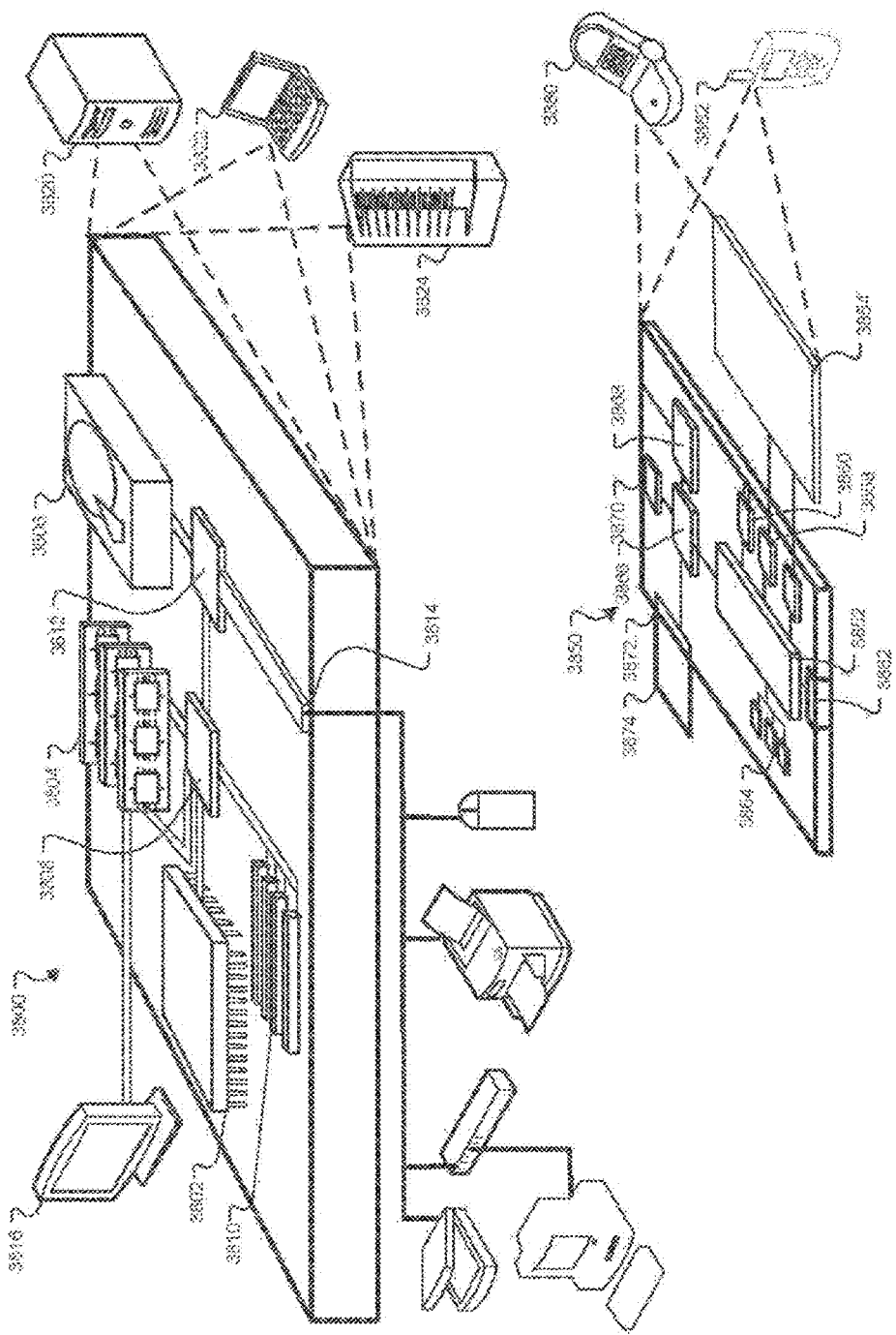
FIG. 38 illustrates an example of a computing device and a mobile computing device that can be used to implement the operations and techniques described herein.

FIG. 38 shows an example of example computer device 3800 and example mobile computer device 3850, which can be used to implement the operations and techniques described herein. For example, a portion or all of the operations of the controller 110 (shown in FIG. 1), the controller 210 (shown in FIG. 2A), the controller 232 (shown in FIG. 2C), or the controller 266 (shown in FIG. 2D) may be executed by the computer device 3800 and/or the mobile computer device 3850. Computing device 3800 is intended to represent various forms of digital computers, including, e.g., laptops, desktops, workstations, personal digital assistants, servers, blade servers, mainframes, and other appropriate computers. Computing device 3850 is intended to represent various forms of mobile devices, including, e.g., personal digital assistants, tablet computing devices, cellular telephones, smartphones, and other similar computing devices. The components shown here, their connections and relationships, and their functions, are meant to be examples only, and are not meant to limit implementations of the techniques described and/or claimed in this document.

Computing device 3800 includes processor 3802, memory 3804, storage device 3806, high-speed interface 3808 connecting to memory 3804 and high-speed expansion ports 3810, and low speed interface 3812 connecting to low speed bus 3814 and storage device 3806. Each of components 3802, 3804, 3806, 3808, 3810, and 3812, are interconnected using various busses, and can be mounted on a common motherboard or in other manners as appropriate. Processor 3802 can process instructions for execution within computing device 3800, including instructions stored in memory 3804 or on storage device 3806 to display graphical data for a GUI on an external input/output device, including, e.g., display 3816 coupled to high speed interface 3808. In other implementations, multiple processors and/or multiple buses can be used, as appropriate, along with multiple memories and types of memory. Also, multiple computing devices 3800 can be connected, with each device providing portions of the necessary operations (e.g., as a server bank, a group of blade servers, or a multi-processor system).

Memory 3804 stores data within computing device 3800. In one implementation, memory 3804 is a volatile memory unit or units. In another implementation, memory 3804 is a non-volatile memory unit or units. Memory 3804 also can be another form of computer-readable medium, including, e.g., a magnetic or optical disk.

Storage device 3806 is capable of providing mass storage for computing device 3800. In one implementation, storage device 3806 can be or contain a computer-readable medium, including, e.g., a floppy disk device, a hard disk device, an optical disk device, or a tape device, a flash memory or other similar solid state memory device, or an array of devices, including devices in a storage area network or other configurations. A computer program product can be tangibly embodied in a data carrier. The computer program product also can contain instructions that, when executed, perform one or more methods, including, e.g., those described above. The data carrier is a computer- or machine-readable medium, including, e.g., memory 3804, storage device 3806, memory on processor 3802, and the like.

High-speed controller 3808 manages bandwidth-intensive operations for computing device 3800, while low speed controller 3812 manages lower bandwidth-intensive operations. Such allocation of functions is an example only. In one implementation, high-speed controller 3808 is coupled to memory 3804, display 3816 (e.g., through a graphics processor or accelerator), and to high-speed expansion ports 3810, which can accept various expansion cards (not shown). In the implementation, low-speed controller 3812 is coupled to storage device 3806 and low-speed expansion port 3814. The low-speed expansion port, which can include various communication ports (e.g., USB, Bluetooth®, Ethernet, wireless Ethernet), can be coupled to one or more input/output devices, including, e.g., a keyboard, a pointing device, a scanner, or a networking device including, e.g., a switch or router, e.g., through a network adapter.

Computing device 3800 can be implemented in a number of different forms, as shown in the figure. For example, it can be implemented as standard server 3820, or multiple times in a group of such servers. It also can be implemented as part of rack server system 3824. In addition or as an alternative, it can be implemented in a personal computer including, e.g., laptop computer 3822. In some examples, components from computing device 3800 can be combined with other components in a mobile device (not shown), including, e.g., device 3850. Each of such devices can contain one or more of computing device 3800, 3850, and an entire system can be made up of multiple computing devices 3800, 3850 communicating with each other.

Computing device 3850 includes processor 3852, memory 3864, an input/output device including, e.g., display 3854, communication interface 3866, and transceiver 3868, among other components. Device 3850 also can be provided with a storage device, including, e.g., a microdrive or other device, to provide additional storage. Each of components 3850, 3852, 3864, 3854, 3866, and 3868, are interconnected using various buses, and several of the components can be mounted on a common motherboard or in other manners as appropriate.

Processor 3852 can execute instructions within computing device 3850, including instructions stored in memory 3864. The processor can be implemented as a chipset of chips that include separate and multiple analog and digital processors. The processor can provide, for example, for coordination of the other components of device 3850, including, e.g., control of user interfaces, applications run by device 3850, and wireless communication by device 3850.

Processor 3852 can communicate with a user through control interface 3858 and display interface 3856 coupled to display 3854. Display 3854 can be, for example, a TFT LCD (Thin-Film-Transistor Liquid Crystal Display) or an OLED (Organic Light Emitting Diode) display, or other appropriate display technology. Display interface 3856 can comprise appropriate circuitry for driving display 3854 to present graphical and other data to a user. Control interface 3858 can receive commands from a user and convert them for submission to processor 3852. In addition, external interface 3862 can communicate with processor 3842, so as to enable near area communication of device 3850 with other devices. External interface 3862 can provide, for example, for wired communication in some implementations, or for wireless communication in other implementations, and multiple interfaces also can be used.

Memory 3864 stores data within computing device 3850. Memory 3864 can be implemented as one or more of a computer-readable medium or media, a volatile memory unit or units, or a non-volatile memory unit or units. Expansion memory 3874 also can be provided and connected to device 3850 through expansion interface 3872, which can include, for example, a SIMM (Single In Line Memory Module) card interface. Such expansion memory 3874 can provide extra storage space for device 3850, or also can store applications or other data for device 3850. Specifically, expansion memory 3874 can include instructions to carry out or supplement the processes described above, and can include secure data also. Thus, for example, expansion memory 3874 can be provided as a security module for device 3850, and can be programmed with instructions that permit secure use of device 3850. In addition, secure applications can be provided through the SIMM cards, along with additional data, including, e.g., placing identifying data on the SIMM card in a secure, non-modifiable manner.

The memory can include, for example, flash memory and/or NVRAM memory, as discussed below. In one implementation, a computer program product is tangibly embodied in a data carrier. The computer program product contains instructions that, when executed, perform one or more methods, including, e.g., those described above. The data carrier is a computer- or machine-readable medium, including, e.g., memory 3864, expansion memory 3874, and/or memory on processor 3852, which can be received, for example, over transceiver 3868 or external interface 3862.

Device 3850 can communicate wirelessly through communication interface 3866, which can include digital signal processing circuitry where necessary. Communication interface 3866 can provide for communications under various modes or protocols, including, e.g., GSM voice calls, SMS, EMS, or MMS messaging, CDMA, TDMA, PDC, WCDMA, CDMA2000, or GPRS, among others. Such communication can occur, for example, through radio-frequency transceiver 3868. In addition, short-range communication can occur, including, e.g., using a Bluetooth®, WiFi, or other such transceiver (not shown). In addition, GPS (Global Positioning System) receiver module 3870 can provide additional navigation- and location-related wireless data to device 3850, which can be used as appropriate by applications running on device 3850. Sensors and modules such as cameras, microphones, compasses, accelerators (for orientation sensing), etc. maybe included in the device.

Device 3850 also can communicate audibly using audio codec 3860, which can receive spoken data from a user and convert it to usable digital data. Audio codec 3860 can likewise generate audible sound for a user, including, e.g., through a speaker, e.g., in a handset of device 3850. Such sound can include sound from voice telephone calls, can include recorded sound (e.g., voice messages, music files, and the like) and also can include sound generated by applications operating on device 3850.

Computing device 3850 can be implemented in a number of different forms, as shown in the figure. For example, it can be implemented as cellular telephone 3880. It also can be implemented as part of smartphone 3882, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to a computer program product, apparatus and/or device (e.g., magnetic discs, optical disks, memory, Programmable Logic Devices (PLDs)) used to provide machine instructions and/or data to a programmable processor, including a machine-readable medium that receives machine instructions.

To provide for interaction with a user, the systems and techniques described here can be implemented on a computer having a display device (e.g., a CRT (cathode ray tube) or LCD (liquid crystal display) monitor) for displaying data to the user and a keyboard and a pointing device (e.g., a mouse or a trackball) by which the user can provide input to the computer. Other kinds of devices can be used to provide for interaction with a user as well; for example, feedback provided to the user can be a form of sensory feedback (e.g., visual feedback, auditory feedback, or tactile feedback); and input from the user can be received in a form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a user interface or a Web browser through which a user can interact with an implementation of the systems and techniques described here), or a combination of such back end, middleware, or front end components. The components of the system can be interconnected by a form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other. In some implementations, the engines described herein can be separated, combined or incorporated into a single or combined engine. The engines depicted in the figures are not intended to limit the systems described here to the software architectures shown in the figures.

What is claimed is:

1. An apparatus comprising:
   a reaction chamber including one or more pairs of electrodes configured to generate a series of electric arcs to synthesize a reactant gas containing at least nitrogen and oxygen to a product gas containing nitric oxide;
   a sensor configured to measure one or more characteristics of the reactant gas or the product gas; and
   a controller in communication with the one or more pairs of electrodes and the sensor, the controller being configured to detect a triggering event based on the one or more characteristics of the reactant gas or the product gas and initiate the series of electric arcs a predetermined amount of time ahead of the triggering event to increase a concentration of nitric oxide in the product gas.

2. The apparatus of claim 1, wherein the predetermined amount of time ahead of the triggering event is configured to be adjusted to control the concentration of nitric oxide in the product gas.

3. The apparatus of claim 1, wherein the one or more characteristics include at least one of a direction of flow of the reactant gas, a tidal volume of a flow of the reactant gas, a timing of a flow of the reactant gas, a change in temperature of a flow of the reactant gas, a change in pressure of the a of the reactant gas, and a flow rate of the reactant gas.

4. The apparatus of claim 1, wherein the one or more characteristics include at least one of timing and volume of an inspiration.

5. The apparatus of claim 4, wherein the predetermined amount of time ahead of the triggering event is adjusted based on the at least one of timing and volume of the inspiration.

6. The apparatus of claim 1, wherein the controller is configured to track at least one of timing and volume of a previous inspiration and predict at least one of timing and volume of a subsequent inspiration.

7. The apparatus of claim 6, wherein the controller is configured to adjust the predetermined amount of time ahead of the triggering event based on the at least one of timing and volume of the subsequent inspiration.

8. An apparatus comprising:
   a reaction chamber including one or more pairs of electrodes configured to generate a series of electric arcs to synthesize a reactant gas containing at least nitrogen and oxygen to a product gas containing nitric oxide, the reaction chamber being at least partially positioned within a tube into which the product gas is delivered;
   a sensor configured to measure one or more characteristics of a flow of a gas in the tube, wherein the one or more characteristics include at least one of volume and timing of inspiration; and
   a controller in communication with the one or more pairs of electrodes and the sensor, the controller being configured to detect a triggering event based on the at least one of volume and timing of inspiration and initiate the series of electric arcs a predetermined amount of time ahead of the triggering event to increase a concentration of nitric oxide in the product gas.

9. The apparatus of claim 8, wherein the predetermined amount of time ahead of the triggering event is configured to be adjusted to control the concentration of nitric oxide in the product gas.

10. The apparatus of claim 8, wherein the one or more characteristics further include at least one of a direction of the flow of the gas, a tidal volume of the flow of the gas, a timing of the flow of the gas, a change in temperature of the flow of the gas, a change in pressure of the flow of the gas, and a flow rate of the flow of gas.

11. The apparatus of claim 8, wherein the tube comprises one of a tracheostomy tube, an endotracheal tube, a nasal tube, a ventilator tube, and an inspiratory line.

12. The apparatus of claim 8, wherein the predetermined amount of time ahead of the triggering event is adjusted based on the at least one of timing and volume of inspiration.

13. The apparatus of claim 8, wherein the controller is configured to track at least one of timing and volume of a previous inspiration and predict at least one of timing and volume of a subsequent inspiration.

14. The apparatus of claim 13, wherein the controller is configured to adjust the predetermined amount of time ahead of the triggering event based on the at least one of timing and volume of the subsequent inspiration.

15. A method for generating nitric oxide comprising:
measuring one or more characteristics of at least one of a flow of reactant gas into a reaction chamber and a flow of product gas out of the reaction chamber;
detecting a triggering event based on the one or more characteristics;
initiating a series of electric arcs in the reaction chamber a predetermined amount of time ahead of the triggering event to synthesize a reactant gas containing nitrogen and oxygen to a product gas containing nitric oxide; and
adjusting the predetermined amount of time ahead of the triggering event to control a concentration of nitric oxide in the product gas.

16. The method of claim 15, wherein the one or more characteristics further include at least one of a direction of the flow of the reactant gas or the flow of product gas, a tidal volume of the flow of the flow of the reactant gas or the flow of product gas, a timing of the flow of the reactant gas or the flow of product gas, a change in temperature of the flow of the reactant gas or the flow of product gas, a change in pressure of the flow of the reactant gas or the flow of product gas, and a flow rate of the flow of the reactant gas or the flow of product gas.

17. The method of claim 15, wherein the one or more characteristics include at least one of timing and volume of an inspiration.

18. The method of claim 17, further comprising adjusting the predetermined amount of time ahead of the triggering event based on the at least one of timing and volume of inspiration.

19. The method of claim 15, further comprising tracking at least one of timing and volume of a previous inspiration and predict at least one of timing and volume of a subsequent inspiration.

20. The method of claim 19, further comprising adjusting the predetermined amount of time ahead of the triggering event based on the at least one of timing and volume of the subsequent inspiration.

* * * * *